US009739734B2

(12) United States Patent
Messerli et al.

(10) Patent No.: US 9,739,734 B2
(45) Date of Patent: Aug. 22, 2017

(54) METHODS AND SYSTEMS OF DETECTING EXOCYTOSIS OF A TARGET MOLECULE FROM A POPULATION OF CELLS

(71) Applicant: THE MARINE BIOLOGICAL LABORATORY, Woods Hole, MA (US)

(72) Inventors: Mark Alan Messerli, Brookings, SD (US); Emma Heart, Tampa, FL (US); Munan Xu, East Falmouth, MA (US); Shanta Menon Messerli, Sioux Falls, SD (US)

(73) Assignee: THE MARINE BIOLOGICAL LABORATORY, Woods Hole, MA (US)

( * ) Notice: Subject to any disclaimer, the term of this patent is extended or adjusted under 35 U.S.C. 154(b) by 0 days.

(21) Appl. No.: 14/889,568

(22) PCT Filed: May 12, 2014

(86) PCT No.: PCT/US2014/037682
§ 371 (c)(1),
(2) Date: Nov. 6, 2015

(87) PCT Pub. No.: WO2014/186282
PCT Pub. Date: Nov. 20, 2014

(65) Prior Publication Data
US 2016/0084782 A1    Mar. 24, 2016

Related U.S. Application Data

(60) Provisional application No. 61/822,639, filed on May 13, 2013.

(51) Int. Cl.
*A61K 35/39* (2015.01)
*G01N 27/02* (2006.01)
*G01N 33/50* (2006.01)
*G01N 33/483* (2006.01)

(52) U.S. Cl.
CPC .......... *G01N 27/026* (2013.01); *A61K 35/39* (2013.01); *G01N 33/4833* (2013.01); *G01N 33/5005* (2013.01)

(58) Field of Classification Search
None
See application file for complete search history.

(56) References Cited

U.S. PATENT DOCUMENTS

2003/0185450 A1* 10/2003 Garakani ............ G06K 9/0014
                                                                       382/232
2006/0085045 A1    4/2006 Harel et al.
2009/0326315 A1    12/2009 Nishi et al.
2012/0190583 A1*  7/2012 Gillis ................ G01N 33/48728
                                                                       506/10
2013/0130299 A1*  5/2013 Dittami ............ G01N 33/48728
                                                                       435/29

FOREIGN PATENT DOCUMENTS

WO    WO-02/077259 A2    10/2002
WO    WO-2013/006683 A2   1/2013

OTHER PUBLICATIONS

Bertrand C. et al. System for Dynamic Measurements of Membrane Capacitance in Intact Epithilial Monolayers. Biophysical J 75(6)2743-56, Dec. 1998.*
Gopel, S. et al. Capacitance Measurements of Exocytosis in Mouse Pancreatic Cells Within Intact Islets of Langerhans. J Physiology 556(3)711-726, May 2004.*
International Preliminary Report on Patentability issued in PCT/US2014/037682 dated Nov. 17, 2015.
C.A. Bertrand et al., "System for Dynamic Measurements of Membrane Capacitance in Intact Epithelial Monolayers", *Biophysical Journal*, vol. 75, No. 6 (1998).
Wei Weng et al., "Monitoring of Vesicular Exocytosis from Single Cells Using Micrometer and Nanometer-Sized Electrochemical Sensors", *Analytical and Bioanalytical Chemistry*, vol. 394, No. 1 (2009).
Kline D et al., "The Timing of Cortical Granule Fusion, Content Dispersal, and Endocytosis during Fertilization of the Hamster Egg: An Electrophysiological and Histochemical Study", *Developmental Biology, Academic Press*, vol. 162, No. 1 (1994).
C. Joshi et al., "Capacitance Measurements. An Analysis of the Phase Detector Technique Used to Study Exocytosis and Endocytosis", *Biophysical Journal*, vol. 53, No. 6 (1988).
Chae Young Cha et al., "Analyzing Electrical Activities of Pancreatic Cells Using Mathematical Models", *Progress in Biophysics and Molecular Biology*, vol. 107, No. 2 (2011).
Leif Oltedal et al., "Transient Release Kinetics of Rod Bipolar Cells Revealed by Capacitance Measurement of Exocytosis from Axon Terminals in Rat Retinal Slices", *The Journal of Physiology*, vol. 588, No. 9 (2010).
International Search Report and Written Opinion issued in PCT/US2014/037682 dated Sep. 5, 2014.

* cited by examiner

*Primary Examiner* — Ralph Gitomer
(74) *Attorney, Agent, or Firm* — Marshall, Gerstein & Borun LLP

(57) ABSTRACT

A method of detecting exocytosis of a target molecule from a population of cells derived from a human subject, includes applying first and second electrical signals, each having a respective frequency, across the population of cells. Each of the first and second electrical signals being either an alternating current or an alternating voltage. The method includes measuring a first voltage change if the first electrical signal is an alternating current or measuring a first current change if the first electrical signal is an alternating voltage, and measuring a second voltage change if the second electrical signal is an alternating current or measuring a second current change if the second electrical signal is an alternating voltage. The method includes determining an electrical impedance of the population of cells, a change in that impedance indicating an amount of the target molecule released from the population of cells.

8 Claims, 7 Drawing Sheets

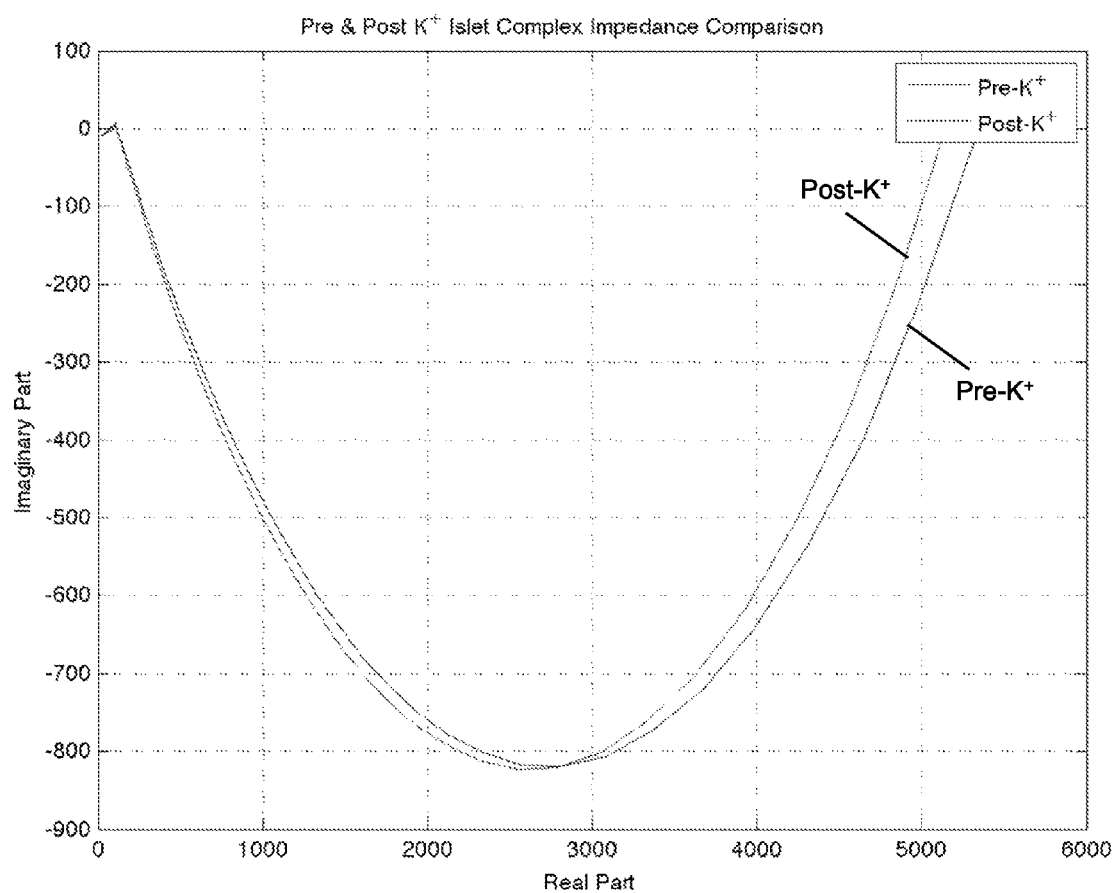

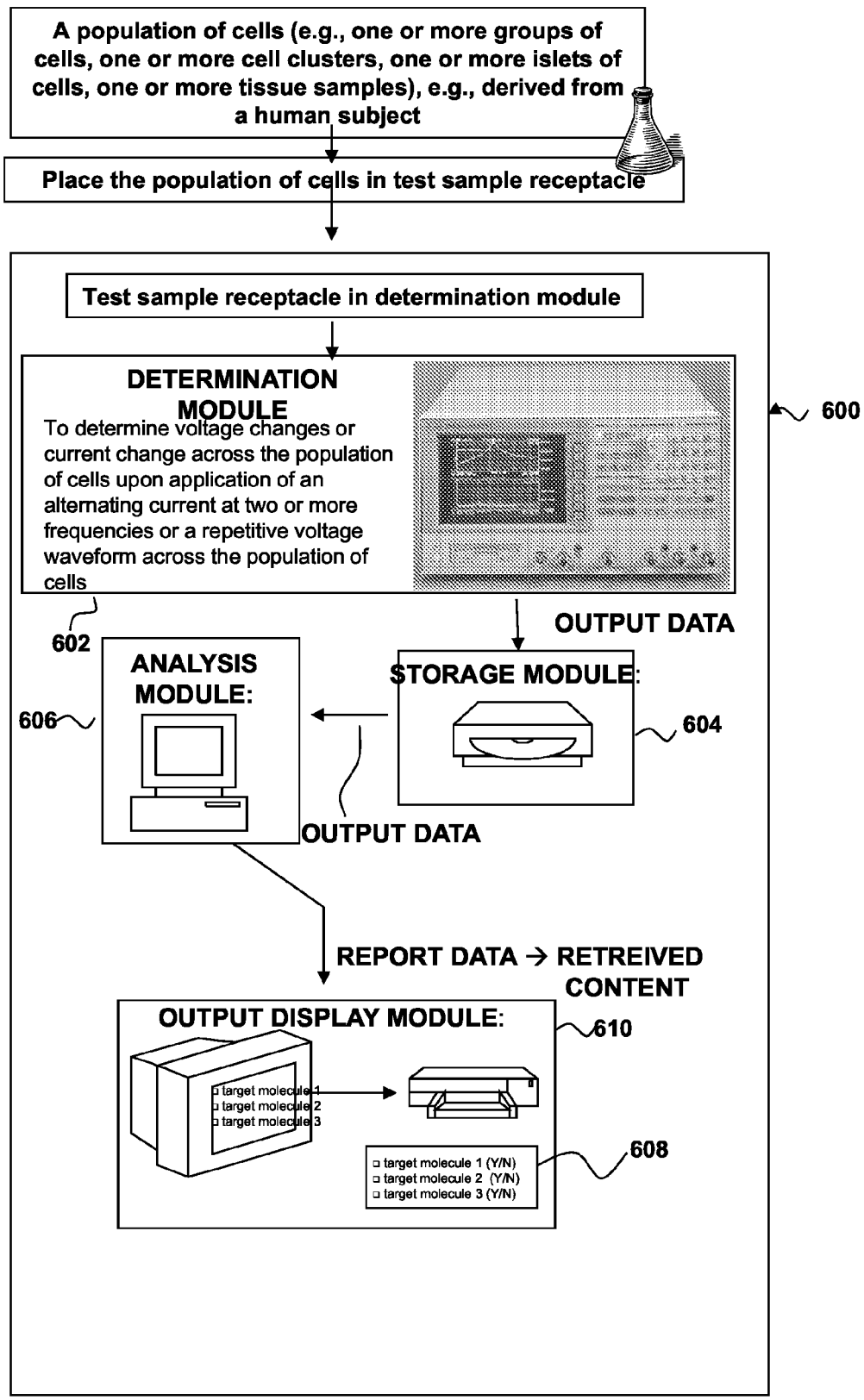

METHODS AND SYSTEMS OF DETECTING EXOCYTOSIS OF A TARGET MOLECULE FROM A POPULATION OF CELLS

GOVERNMENT SUPPORT

This invention was made with government support under grant No. R56DK088093 awarded by the National Institutes of Health (NIH). The U.S. government has certain rights in the invention.

TECHNICAL FIELD

Described herein relates generally to methods and systems for detecting exocytosis of a target molecule from a population of cells, a cell cluster, a cell islet, or a tissue sample.

BACKGROUND

Pancreatic islet transplantation is a surgical solution to type I diabetes. Continued efforts in optimizing islet isolation, transport, transplantation and survivability after transplantation are required to increase efficiency and efficacy of the pancreatic islet transplantation procedure. Additionally, increased throughput of pharmacological screens on rare tissue (e.g., human islets) is required for advancing treatments of type II diabetes. While the ultimate test of islet function is the ability to release insulin in response to glucose stimulation, there is yet no effective method to assess insulin exocytosis at the whole islet level. Accordingly, there is a need for scalable and sensitive methods and/or systems to assess and/or monitor insulin exocytosis at the whole islet level.

SUMMARY

Embodiments of various aspects described herein are, at least in part, based on discovery and development of a simple and sensitive method for high throughput screening of insulin exocytosis at the whole islet level using impedance analysis. Plasma membranes generally possess an electrical capacitance of about 1 $\mu F/cm^2$, and insulin secretory vesicles possess a capacitance of about 3 fF. Thus, exocytosis of insulin can lead to an increase in plasma membrane capacitance for extended periods of time. In some embodiments, the inventors applied an alternating current at two frequencies or a repetitive voltage waveform (e.g., a repetitive square voltage waveform) to a pancreatic islet and surprisingly detected an immediate change in whole islet capacitance, which corresponds to exocytosis of a target molecule (e.g., insulin), after stimulation of the pancreatic islet with an insulin secretagogue (e.g., a salt such as potassium chloride or glucose). By modeling the whole islet as an equivalent electrical circuit, the inventors performed impedance analysis of the electrical circuit, which enables separation of resistance and capacitances and characterization of the actual values in the circuit. Impedance analysis is typically performed on single cells using amplifiers; however, it has never been used to detect exocytosis of a molecule (e.g., insulin) at the whole islet level or based on a population of cells (e.g., a cell cluster or a tissue sample), in which intracellular space and/or organization/arrangement of the cells within the population can additionally contribute a significance to the impedance analysis. Accordingly, the inventors have discovered inter alia a novel impedance spectroscopy-based method to detect exocytosis of a target molecule from a population of cells, a cell cluster, an islet of cells, or a tissue sample. Thus, embodiments of various aspects provided herein relate to methods and systems for detecting exocytosis of a target molecule from a population of cells (including a cell cluster, an islet of cells, or a tissue sample), and applications thereof.

In one aspect, methods of detecting exocytosis or endocytosis of a target molecule from or into a population of cells (e.g., a group of cells, one or more cell clusters, one or more islets of cells, or one or more tissue samples) are provided herein. The method comprises (a) applying a first alternating current with a first frequency across the population of cells; (b) applying a second alternating current with a second frequency across the population of cells; (c) measuring a first voltage change across the population of cells at the first frequency; (d) measuring a second voltage change across the population of cells at the second frequency; and (e) determining an electrical impedance of the population of cells, wherein a change in the electrical impedance of the population of cells indicates an amount of the target molecule released from or entered into the population of cells.

In some embodiments, the determination of the electrical impedance of the population of cells can comprise matching a best-fitting line each computed for the measured first voltage change and the second voltage change to a function described by an equivalent electric circuit modeling the population of cells, wherein the equivalent electric circuit comprises a plurality of passive elements and at least one of the passive elements is a capacitor representing sum of plasma membrane capacitances of all cells in the population, thereby determining at least a change in impedance of the capacitor provides an indication of an amount of the target molecule released from or entered into the population of cells.

In order to compute at least the impedance of the capacitor representing sum of plasma membrane capacitances of all cells in the population, in some embodiments, the measured voltage change can be separated into a first component that is in phase with the applied current, and a second component that is out of phase with the applied current. The first component of the measured voltage change generally corresponds to a voltage change across a resistor, while the second component of the measured voltage change generally corresponds to a voltage change across the capacitor.

In accordance with this aspect described herein, the first alternating current and second alternating current can be applied at their respective frequencies to the population of cells simultaneously or separately (e.g., one frequency at a time). While said at least two alternating currents can be applied to the population of cells separately, in one embodiment, simultaneous application of at least two alternating currents to the population of cells can provide a better real-time assessment for exocytosis. Accordingly, in one embodiment, the first alternating current and second alternating current are applied at their respective frequencies to the population of cells simultaneously.

The amplitude or amount of the first alternating current and second alternating current applied to the population of cells should not produce any adverse effect on the cells, e.g., heating of the culture medium, or causing cell death, or induce any electrical excitation of the cells. The amplitude or amount of the first alternating current and second alternating current can vary depending on the conductance around the cells. In one embodiment, the amplitude or amount of the first alternating current and second alternating current applied to the population of cells is the minimum amount of current that can provide a sufficient signal to noise ratio for detection. In some embodiments, the amplitude or amount of the first alternating current and second alternating current applied to the population of cells is less than the current that is capable of electrically exciting the cells.

The frequency of the first alternating current and the second alternating current applied to the population of cells can be of any value, provided that exocytosis of a target molecule can be detected at a selected frequency, e.g., a shift representing exocytosis is detectable in a complex impedance plot, e.g., as shown in FIG. 3. In one embodiment, an optimal frequency is selected when the largest shift (e.g., before and after stimulation with a secretagogue) is observed in the corresponding complex impedance plot. In some embodiments, the frequency of the first alternating current and the second alternating current can range from about 10 Hz to about 10 MHz, or from about 100 Hz to about 1 MHz, or from about 1 kHz to about 1000 kHz. The optimal frequency of the alternating currents applied to the population of cells can vary with a number of factors, including, but not limited to types and/or size of cell population, target molecule to be detected and/or potency of a secretagogue if added.

In another aspect, methods based on application of a repetitive voltage waveform, instead of an alternating current (e.g., a sinusoidal current) at two frequencies as described above, to a population of cells are provided herein. In this aspect, the method of detecting exocytosis or endocytosis of a target molecule from or into a population of cells comprises (a) applying a repetitive voltage waveform across the population of cells; (b) measuring a current change across the population of cells; and (c) determining an electrical impedance of the population of cells, wherein a change in the electrical impedance of the population of cells indicates an amount of the target molecule released from or entered into the population of cells.

While any repetitive voltage waveform in any shape can be provided to the population of cells, in one embodiment, the repetitive voltage waveform is a repetitive voltage square waveform. Without wishing to be bound by theory, when there is sufficient extracellular impedance, the square wave can enable more thorough characterization of the passive electrical elements, as the square wave can be modeled as a number of sine waves with different frequencies and amplitudes, that is, there can be more information contained in the simple square wave.

The repetitive voltage waveform can have a period and/or amplitude optimized to yield the best signal to noise ratio without over sampling or damaging the cells.

In some embodiments, the determination of the electrical impedance of the population of cells can comprise matching a best-fitting line each computed for the measured current change to a function described by an equivalent electric circuit modeling the population of cells, wherein the equivalent electric circuit comprises a plurality of passive elements and at least one of the passive elements is a capacitor representing sum of plasma membrane capacitances of all cells in the population, thereby determining at least a change in impedance of the capacitor provides an indication of an amount of the target molecule released from or entered into the population of cells.

In some embodiments, computation of at least the impedance of the capacitor representing sum of plasma membrane capacitances of all cells in the population requires separation of the measured current change into a first component that is in phase with the applied voltage waveform and a second component that is out of phase with the applied voltage waveform, wherein the first component of the measured current change corresponds to a current change across a resistor, and the second component of the measured current change corresponds to a current change across the capacitor.

In some embodiments of various aspects described herein, the methods can further comprise contacting the population of cells with an agent identified for or being assessed for modulating exocytosis or endocytosis of a target molecule, e.g., prior to application of a alternating current (e.g., an alternating current) at two or more frequencies, or a repetitive voltage waveform. In these embodiments, the methods can be used to evaluate an effect of the agent on exocytosis or endocytosis of a target molecule from or into the population of cells. In some embodiments, the methods can be used to assess the potency and/or viability of the population of cells based on degree of exocytosis of a target molecule, e.g., after stimulation of the population of cells with a known secretagogue for the target molecule.

Accordingly, in yet another aspect, methods for assessing viability of a population are provided herein, wherein the method comprises performing one or more embodiments of the methods described herein for detecting exocytosis of a target molecule from a population of cells.

A further aspect provides a method of treating a subject with diabetes comprising transplanting into the subject at least one islet determined to be potent based on assessment of release of insulin from the islet using one or more embodiments of the methods described herein.

Methods of identifying an agent for modulating exocytosis of a target molecule (e.g., a secretagogue) from cells are also provided herein. The method comprises (a) contacting a population of cells with a candidate agent; (b) performing one or more embodiments of the methods described herein to detect exocytosis of the target molecule from the population of cells; and (c) comparing the electrical impedance of the population of cells determined from step (b) with a control, wherein a change in the electrical impedance of the population of cells from the control indicates an effect of the candidate agent on modulating the exocytosis of the target molecule; thereby identifying the candidate agent for modulating the exocytosis of the target molecule from the cells.

In some embodiments, the methods of identifying a secretagogue can be used to identify an agent for enhancing exocytosis of insulin. For example, in these embodiments, the population of cells used for identifying an insulin secretagogue can be insulin-secreting cells such as a pancreatic islet, a population of beta cells, and/or insulin-secreting stem cells. In some embodiments, the selected insulin secretagogue can be used for treatment of diabetes in a subject.

Systems (e.g., a computer system) which can be employed in methods of various aspects described herein are also provided. In this aspect, the system comprises:
(a) at least one determination module configured to receive a population of cells and perform the following:
  i. applying a first alternating current with a first frequency across the population of cells;
  ii. applying a second alternating current with a second frequency across the population of cells;
  iii. measuring a first voltage change across the population of cells at the first frequency;
  iv. measuring a second voltage change across the population of cells at the second frequency; and
(b) at least one storage device configured to store the first voltage change and the second voltage change determined from said determination module;

(c) at least one analysis module configured to determine an electrical impedance of the population of cells based the measurements of the first voltage change and the second voltage change determined from the determination module, wherein a change in the electrical impedance of the population of cells indicates an amount of a target molecule released from or entered into the population of cells; and (d) at least one display module for displaying a content based in part on the analysis output from said analysis module, wherein the content comprises a signal indicative of the amount of the target molecule released from or entered into the cells.

In some embodiments, said at least one analysis module can be further configured to match a best-fitting line each computed for the measured first voltage change and the second voltage change to a function described by an equivalent electric circuit modeling the population of cells, wherein the equivalent electric circuit comprises a plurality of passive elements and at least one of the passive elements is a capacitor representing sum of plasma membrane capacitances of all cells in the population, thereby determining at least a change in impedance of the capacitor provides an indication of an amount of the target molecule released from or entered into the population of cells.

In some embodiments, said at least one analysis module can be further configured to separate the measured voltage change into a first component in phase with the applied current and a second component out of phase with the applied current, wherein the first component of the measured voltage change corresponds to a voltage change across a resistor, and the second component of the measured voltage change corresponds to a voltage change across the capacitor.

In some embodiments, said at least one determination module can be configured to apply to the population of cells the first alternating current and second alternating current simultaneously. In alternative embodiments, said at least one determination module can be configured to apply to the population of cells the first alternating current and second alternating current separately or sequentially. The frequency of the first alternating current and the second alternating current applied to the population of cells can be of any value, provided that exocytosis of a target molecule can be detected at a selected frequency, e.g., a shift representing exocytosis is detectable in a complex impedance plot, e.g., as shown in FIG. 3. In one embodiment, an optimal frequency is selected when the largest shift (e.g., before and after stimulation with a secretagogue) is observed in the corresponding complex impedance plot. In some embodiments, the frequency of the first alternating current and the second alternating current can range from about 10 Hz to about 10 MHz, or from about 100 Hz to about 1 MHz, or from about 1 kHz to about 1000 kHz. The optimal frequency of the alternating currents applied to the population of cells can vary with a number of factors, including, but not limited to types and/or size of cell population, target molecule to be detected and/or potency of a secretagogue if added. The frequency of the first alternating current and the second alternating current applied to the population of cells can be the same or different. For example, when the first alternating current and the second alternating current apply substantially the same frequency to the population of cells, it is contemplated that a more complex circuit model may be needed. Alternatively, when the first alternating current and the second alternating current apply different frequencies to the population of cells, a simple electric circuit (e.g., but not limited to, a 3-passive element circuit model) can be used.

A system based on application of a repetitive voltage waveform to a population of cells is also provided herein. The system comprises:

(a) at least one determination module configured to receive a population of cells and perform the following:
  i. applying a repetitive voltage waveform across the population of cells;
  ii. measuring a current change across the population of cells; and (b) at least one storage device configured to store the current change determined from said determination module;

(c) at least one analysis module configured to determine an electrical impedance of the population of cells based the measurements of the current change determined from the determination module, wherein a change in the electrical impedance of the population of cells indicates an amount of a target molecule released from or entered into the population of cells; and (d) at least one display module for displaying a content based in part on the analysis output from said analysis module, wherein the content comprises a signal indicative of the amount of the target molecule released from or entered into the cells.

In some embodiments, said analysis module can be further configured to match a best-fitting line each computed for the measured first voltage change and the second voltage change to a function described by an equivalent electric circuit modeling the population of cells, wherein the equivalent electric circuit comprises a plurality of passive elements and at least one of the passive elements is a capacitor representing sum of plasma membrane capacitances of all cells in the population, thereby determining at least a change in impedance of the capacitor provides an indication of an amount of the target molecule released from or entered into the population of cells.

In some embodiments, said analysis module can be further configured to separate the measured current change into a first component in phase with the applied voltage waveform and a second component out of phase with the applied voltage waveform, wherein the first component of the measured current change corresponds to a current change across a resistor, and the second component of the measured current change corresponds to a current change across the capacitor.

Any art-recognized voltage waveform can be generated in said at least one determination module and applied to the population of cells. In one embodiment, said at least one determination module can be configure to generate a repetitive voltage square waveform.

In some embodiments of the systems of various aspects described herein, said at least one determination module can be further configured to perform an act of contacting the population of cells with an agent identified for or being assessed for modulating exocytosis of the target molecule released from or entered into the population of cells, e.g., prior to applying to a population of cells a alternating current at two or more frequencies or a repetitive voltage waveform.

In some embodiments where the population of cells is contacted with an agent, said at least one analysis module can be further configured to compare the electrical impedance of the population of cells with a control determined from the determination module or stored in the storage device, wherein a change in the electrical impedance of the population of cells from the control indicates an effect of the agent on modulating the exocytosis of the target molecule. In these embodiments, the content can further comprise a signal indicative of the agent selected for modulating exocytosis of the target molecule. In some embodiments, the agent can be identified for enhancing exocytosis of insulin, e.g., which can be used for treatment of diabetes in a subject.

In some embodiments, the change in the electrical impedance of the population of cells and/or the amount of the target molecule released from or entered into the cells as determined in the analysis module can provide assessment of viability of the population of cells. In these embodiments, the content can further comprise a signal indicative of viability of the population of cells.

In some embodiments where the population of cells is a pancreatic islet, the change in the electrical impedance of the pancreatic islet and/or the amount of insulin released from the pancreatic islet as determined in the analysis module can provide assessment of potency of the pancreatic islet. In these embodiments, the content can further comprise a signal indicative of the pancreatic islet recommended or not recommended for transplantation into a subject with diabetes.

In accordance with different aspects described herein, various components of the population of cells (including, e.g., plasma membranes, cytosolic space within the cells, and intercellular space between the cells) can contribute to electrical impedance of the population, and be modeled as a passive component (e.g., a resistor, a capacitor, or a combination thereof) in the equivalent electric circuit accordingly. Thus, the equivalent electric circuit used in modeling the population of cells for determination of its electrical impedance comprises a plurality of passive elements (e.g., at least one resistor, at least one capacitor, or any combination thereof). For example, in some embodiments, the plurality of passive elements can comprise at least one or more (e.g., 1, 2, 3, 4, 5, 6, or more) capacitors. In some embodiments, the equivalent electric circuit can further comprise at least one or more (e.g., 1, 2, 3, 4, 5, 6, or more) resistors.

Each single cell within the population can be modeled independently as a smaller electric circuit, which is then connected with others to form a complex equivalent electric circuit, or alternatively, the entire population of cells can be modeled as a whole entity.

In some embodiments of the methods and systems described herein, the entire population of cells can be modeled as a whole entity. For example, in some embodiments, at least one of the passive elements is a capacitor representing the combined plasma membrane capacitances of all cells in the population. In some embodiments, the combined plasma membrane capacitances of the population of cells can be modeled as a combination of a capacitor and a first resistor (e.g., connected in parallel to each other in the equivalent electric circuit). In some embodiments, the combined cytosolic space of the population of cells is modeled as a second resistor. In these embodiments, the second resistor can be connected in series with at least the capacitor (representing the plasma membrane capacitances) in the equivalent electric circuit. In some embodiments, the intercellular space of the population of cells can be modeled as a third resistor, e.g., which can be connected in parallel to the second resistor in the equivalent electric circuit.

Analysis of impedance spectroscopy data to determine impedance of the resistors and capacitors within an equivalent electric circuit are known in the art. In general, the impedance of resistors (e.g., first, second, or third resistor herein) can be determined from the first component of the measured voltage or current change that is in phase with the applied current or voltage waveform, respectively; while impedance of a capacitor can be determined from the second component of the measured voltage or current change that is out of phase with the applied current or voltage waveform, respectively.

The methods and systems described herein can be used to detect exocytosis of any target molecule that is a secretory molecule for a target population of cells, and can cause a change in the plasma membrane capacitance during exocytosis. In some embodiments, the target molecule can be a secretory hormone. Examples of a secretory hormone can include, but are not limited to, insulin, glucagon, somatostatin, or any combination thereof.

The population of cells that are amenable to the methods and systems described herein can comprise one or more population of single cells, one or more cell clusters, one or more islets of cells, one or more tissue samples, or any combinations thereof. The population of cells can be derived from any tissue type. In one embodiment, the population of cells is derived from a pancreatic tissue. For example, the population of cells can comprise a pancreatic islet (e.g., an islet comprising a population of alpha cells, beta cells, and gamma cells), insulin-secreting beta cells, or insulin-secreting stem cells. The population of cells can be derived from any source, e.g., in vitro (e.g., cultured cells including, e.g., genetically-engineered cells), ex vivo, or in vivo. In some embodiments, the population of cells can be derived from a human subject.

Not only can the methods and systems described herein be used for detecting exocytosis of a target molecule from a population of cells, in some embodiments, the methods and systems described herein can also be adapted to assess and sort human pancreatic islets prior to transplantation, which can in turn advance islet transplantation procedures, and/or to screen for treatments of diabetes by monitoring functional release of insulin from islets upon exposure to a candidate agent.

BRIEF DESCRIPTION OF THE DRAWINGS

FIG. 1A is a schematic diagram showing application of an AC current to an islet. FIG. 1B is a schematic diagram of an equivalent 4-passive element circuit model of an islet. An AC current flowing through $R_{MEM}$, $C_{MEM}$, $R_{CYT}$, $R_{INT}$ can result in a voltage drop across each of these elements. The magnitude and phase of the measured voltage drops for both applied frequencies provides information to calculate $R_{MEM}$, $C_{MEM}$, $R_{CYT}$, and $R_{INT}$. FIG. 1C is a schematic diagram of an equivalent 3-passive element circuit model of an islet. An AC current flowing through $C_{MEM}$, $R_{CYT}$, $R_{INT}$ can result in a voltage drop across each of these elements. The magnitude and phase of the measured voltage drops for both applied frequencies provides information to calculate $C_{MEM}$, $R_{CYT}$, and $R_{INT}$.

FIG. 3 is an overlay of two complex impedance plot (CIP) showing changes in impedance at one frequency before (blue) and after (red) addition of 25 mM KCl as an insulin secretagogue that produces substantial exocytosis of insulin from cells in the islet. The shift after addition of 25 mM KCl is due to exocytosis of insulin as well as an increase in the plasma membrane surface area and capacitance. The units on the complex impedance plot represent the impedance of the real (resistance) and imaginary (capacitance) properties of the pancreatic islets with relative units that have not been normalized to Ohms.

FIG. 4A is a graph of time-series impedance measurements showing the real (whole islet resistance) component of the islet circuit. FIG. 4B is a graph of time-series impedance measurements showing the imaginary (whole islet capacitance) component of the islet circuit. In the beginning of the recording a background signal indicates inactive exocytotic activity of the islet. Addition of KCl to a final concentration of 25 mM leads to an immediate change in whole islet capacitance (FIG. 4B) but not whole islet resistance (FIG. 4A). The units on the y-axis in FIGS. 4A-4B are listed as 10 times the percentage change in whole islet capacitance acquired at a frequency of ~1250 Hz. The capacitance plateaus before starting another slight rise. The change in capacitance is directly proportional to the amount of insulin that this islet released.

FIG. 5 is a block diagram showing an exemplary system that can be for use in the methods described herein, e.g., for detecting exocytosis or endocytosis of a target molecule from or into a population of cells.

DETAILED DESCRIPTION OF THE INVENTION

Figures 1A, 1B, 1C:
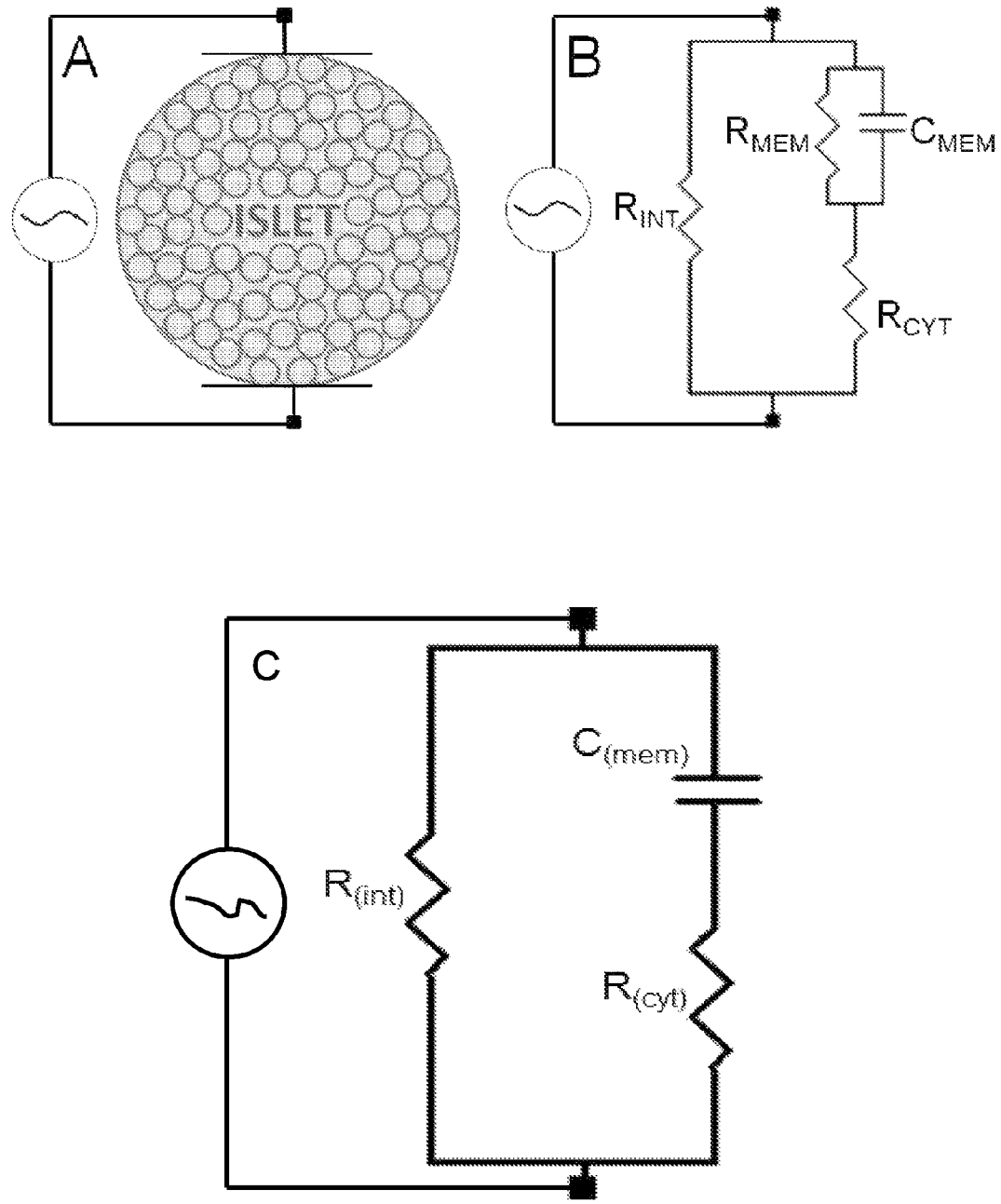
FIGS. 1A-1C are schematic diagrams showing application of an AC current with two different frequencies to an islet.

Embodiments of various aspects described herein are, at least in part, based on discovery and development of a simple and sensitive method for high throughput screening of insulin exocytosis at the whole islet level using impedance analysis. Insulin exocytosis is a process which transiently increases plasma membrane surface area. The plasma membrane (PM) functions in part as an electrical capacitor (~1 g/cm$^2$), and plasma membrane capacitance (PMc) is directly proportional to the area of the PM. Transient increases in PM surface area due to the fusion of insulin granules, and may be followed using electrical capacitance measurements and real-time measurement of PMc serves to monitor insulin vesicle fusion events in single β-cells. Typical measurement of PMc is currently performed by measurement of "impedance" (alternating current (AC) analog of direct current DC "resistance"). This method is applied invasively by whole cell voltage clamp via a single patch pipette, and can be performed on individual β-cells only. However, the single β-cell does not adequately reflect the behavior of the entire β-cell population in an islet, especially when considering the diseased state.

In contrast to the existing invasive single-cell patch clamp approach, presented herein is a novel method of detecting exocytosis of a molecule from a population of cells (e.g., a cell cluster, an islet of cells, or a small tissue) that can eliminate the need for the invasive patch clamp approach and single-cell limitation. In particular, the inventors applied an alternating current at two frequencies or a repetitive voltage waveform (e.g., a repetitive square voltage waveform) to a pancreatic islet and surprisingly detected an immediate change in whole islet capacitance, which corresponds to exocytosis of a target molecule (e.g., insulin), after stimulation of the pancreatic islet with an insulin secretagogue (e.g., a salt such as potassium chloride or glucose). By modeling the whole islet as an equivalent electrical circuit, the inventors performed impedance analysis of the electrical circuit, which enables separation of resistance and capacitances and characterization of the actual values in the circuit. Impedance analysis is typically performed on single cells using amplifiers; however, it has never been used to detect exocytosis of a molecule (e.g., insulin) at the whole islet level or based on a population of cells (e.g., a cell cluster or a tissue sample), in which intracellular space and/or organization/arrangement of the cells within the population can additionally contribute a significance to the impedance analysis. Accordingly, the inventors have discovered inter alia a novel impedance spectroscopy-based method to detect exocytosis of a target molecule from a population of cells, a cell cluster, an islet of cells, or a tissue sample. Thus, embodiments of various aspects provided herein relate to methods and systems for detecting exocytosis or endocytosis of a target molecule from or into a population of cells (including a cell cluster, an islet of cells, or a tissue sample), and applications thereof.

Methods of Detecting Exocytosis of a Target Molecule from a Population of Cells or Endocytosis of a Target Molecule into a Population of Cells In one aspect, the method described herein employs use of Dual Frequency Impedance Spectroscopy (DFIS) to determine impedance measurement of the entire population of cells (e.g., but not limited to, one or more groups of cells, one or more cell clusters, one or more whole islets of cells, or one or more tissue samples). The method comprises (a) applying a first alternating current with a first frequency across the population of cells; (b) applying a second alternating current with a second frequency across the population of cells; (c) measuring a first voltage change across the population of cells at the first frequency; (d) measuring a second voltage change across the population of cells at the second frequency; and (e) determining an electrical impedance of the population of cells, wherein a change in the electrical impedance of the population of cells indicates an amount of the target molecule released from or entered into the population of cells. In one embodiment, the method can be used for real-time recording of whole islet insulin exocytosis.

As used herein, the term "alternating current" refers to an electric current that reverse its direction at regular or irregular intervals. An alternating current can be in any alternating waveform, e.g., but not limited to, a sine wave, a triangular wave, a square wave, or an arbitrary periodic waveform. In some embodiments, the alternating current is a sinusoidal current, which is an alternating current that constitutes a sinusoidal function of time, e.g., in the form $i = I_m \sin(\omega t + \Phi)$, where i is the instantaneous value of the current, $I_m$ is the current's amplitude, $\omega$ is the angular frequency, and $\Phi$ is the initial phase angle. In other embodiments, the alternating current can be a non-sinusoidal current.

At least two or more alternating currents (including, e.g., at least 3, at least 4, at least 5, or more alternating currents) can be applied at their respective frequencies to the population of cells simultaneously or separately (e.g., one frequency at a time). While said at least two alternating currents can be applied to the population of cells separately, in one embodiment, simultaneous application of at least two alternating currents to the population of cells can provide a better real-time assessment for exocytosis. For example, if one frequency was applied at a time, certain assumptions would be required. Exemplary assumptions include, e.g., (1) that exocytosis events would be long lived (e.g., for beta cells they are), and/or (2) that substantial changes in conductance and capacitance did not occur between the measurements.

One of the advantages of applying to the population of cells at least two or more frequencies is that changes in conductance from the capacitance can be separated out. Accordingly, in one embodiment, the first alternating current and second alternating current are applied at their respective frequencies to the population of cells simultaneously.

The amplitude or amount of the first alternating current and second alternating current applied to the population of cells should not produce any adverse effect on the cells, e.g., heating of the culture medium, or causing cell death, or induce any electrical excitation of the cells. In general, the amplitude or amount of the first alternating current and second alternating current applied to the population of cells can vary depending on the conductance around the cells. In one embodiment, the amplitude or amount of the first alternating current and second alternating current applied to the population of cells is the minimum amount of current that can provide a sufficient signal to noise ratio for detection. In some embodiments, the amplitude or amount of the first alternating current and second alternating current applied to the population of cells is less than the current that is capable of electrically exciting the cells.

The frequency of at least two alternating currents (e.g., first alternating current and the second alternating current) applied to the population of cells can be of any value, provided that exocytosis of a target molecule can be detected at a selected frequency, e.g., a shift representing exocytosis is detectable in a complex impedance plot, e.g., as shown in FIG. 3. In one embodiment, an optimal frequency is selected when the largest shift (e.g., before and after stimulation with a secretagogue) is observed in the corresponding complex impedance plot. Stated another way, in order to optimize the resolution for monitoring changes in electrical impedance of the population of cells (e.g., the combined plasma membrane capacitances of all cells within the population), an appropriate alternating current (AC) can be applied at selected frequencies where the measured voltage drop across the population of cells is readily detectable (e.g., where the measured voltage drop across the population of cells changes the most) during exocytosis. By way of example only, optimal AC frequencies can be identified as follows: Complex Impedance Plots (CIP) are generated by graphing the magnitude of the real vs. the imaginary parts of the impedance for a range of applied AC frequencies to the population of cells in the presence of a secretagogue of interest (e.g., glucose). CIP can provide visualization of the changes in plasma membrane capacitance (PMc) over the range of applied frequencies, and thus the frequencies (e.g., 2 frequencies or more) at which the largest changes (e.g., the two largest changes) in plasma membrane capacitance can be determined as optimal AC frequencies.

The application of alternating currents at two or more frequencies across the population of cells can be performed via electrodes. For example, a population of cells can be sandwiched between and contacted with two pairs of electrodes, which are connected to an art-recognized impedance analyzer for impedance measurement, wherein a source electrode in each pair provides an alternating current at a selected frequency, and the corresponding voltage change (e.g., a voltage drop) across the population of cells is then measured with a recording electrode in each pair.

In some embodiments, the determination of the electrical impedance of the population of cells can comprise computing a best-fitting line each for the measured first voltage change and the second voltage change. The best-fit to a series of the first and/or second voltage change measurements can be performed by any methods known in the art, e.g., by linear regression, or non-linear least square fitting (e.g., but not limited to, a polynomial, a curve (e.g., circular, semi-circular, elliptical, parabolic, and hyperbolic arcs), a trigonometric function (such as sine and cosine), or any combinations thereof).

In some embodiments, the determination of the electrical impedance of the population of cells can comprise modeling the population of cells as an equivalent electric circuit comprising a plurality of passive elements, which is further described in detail below. By matching the best-fitting line each for the measured first voltage change and second voltage change to a function described by the equivalent electric circuit modeling the population of cells, the impedance of the passive elements can be determined. In some embodiments, at least one of the passive elements is a capacitor representing sum of plasma membrane capacitances of all cells in the population, thereby determining at least a change in impedance of the capacitor provides an indication of an amount of the target molecule released from or entered into the population of cells.

In order to compute at least the impedance of the capacitor representing sum of plasma membrane capacitances of all cells in the population, in some embodiments, the measured voltage change can be separated into a first component that is in phase with the applied current, and a second component that is out of phase with the applied current. The first component of the measured voltage change generally corresponds to a voltage change across a resistor, while the second component of the measured voltage change generally corresponds to a voltage change across the capacitor.

In another aspect, methods based on application of a repetitive voltage waveform, instead of an alternating current (e.g., a sinusoidal current) at two frequencies as described above, to a population of cells are provided herein. In this aspect, the method of detecting exocytosis or endocytosis of a target molecule from or into a population of cells comprises (a) applying a repetitive voltage waveform across the population of cells; (b) measuring a current change across the population of cells; and (c) determining an electrical impedance of the population of cells, wherein a change in the electrical impedance of the population of cells indicates an amount of the target molecule released from or entered into the population of cells.

While any repetitive voltage waveform in any shape (e.g., but not limited to, a square wave, a triangle wave, a saw tooth wave) can be provided to the population of cells, in one embodiment, the repetitive voltage waveform is a repetitive voltage square waveform. Without wishing to be bound by theory, when there is sufficient extracellular impedance, the square wave can enable more thorough characterization of the passive electrical elements, as the square wave can be modeled as a number of sine waves with different frequencies and amplitudes, that is, there can be more information contained in the simple square wave.

The repetitive voltage waveform can have a period and/or amplitude optimized to yield the best signal to noise ratio without over sampling or damaging the cells.

As used herein, the term "repetitive voltage waveform" refers to a voltage waveform that repeats itself at regular or arbitrary intervals. In some embodiments, the voltage can reverse its polarity at regular or arbitrary intervals. In alternative embodiments, the voltage can have a constant polarity.

In some embodiments, the determination of the electrical impedance of the population of cells can comprise computing a best-fitting line for the measured current change. The best-fit to a series of the current change measurements can be performed by any methods known in the art, e.g., by linear regression, or non-linear least square fitting (e.g., but not limited to, a polynomial, a curve (e.g., circular, semicircular, elliptical, parabolic, and hyperbolic arcs), a trigonometric function (such as sine and cosine), or any combinations thereof).

In some embodiments, the determination of the electrical impedance of the population of cells can comprise modeling the population of cells as an equivalent electric circuit comprising a plurality of passive elements, which is further described in detail below. By matching the best-fitting line for the measured current change to a function described by the equivalent electric circuit modeling the population of cells, the impedance of the passive elements can be determined. In some embodiments, at least one of the passive elements is a capacitor representing sum of plasma membrane capacitances of all cells in the population, thereby determining at least a change in impedance of the capacitor provides an indication of an amount of the target molecule released from or entered into the population of cells.

In some embodiments, computation of at least the impedance of the capacitor representing sum of plasma membrane capacitances of all cells in the population requires separation of the measured current change into a first component that is in phase with the applied voltage waveform and a second component that is out of phase with the applied voltage waveform, wherein the first component of the measured current change corresponds to a current change across a resistor, and the second component of the measured current change corresponds to a current change across the capacitor.

In some embodiments of various aspects described herein, the methods can further comprise contacting the population of cells with an agent identified for or being assessed for modulating exocytosis or endocytosis of a target molecule, e.g., prior to application of an alternating current (e.g., an alternating current) at two or more frequencies, or a repetitive voltage waveform. In these embodiments, the methods can be used to evaluate an effect of the agent on exocytosis of a target molecule from the population of cells or on endocytosis of a target molecule into the population of cells. In some embodiments, the methods can be used to assess the potency and/or viability of the population of cells based on degree of exocytosis of a target molecule, e.g., after stimulation of the population of cells with a known secretagogue for the target molecule.

For a population of cells that comprise more than one different cell types contributing to the plasma membrane capacitance (PMc), in some embodiments, it is desirable to contact the population of cells with an agent specific for stimulating endocytosis or exocytosis of a target molecule and/or specific for stimulating target cells such that any change in the plasma membrane capacitance measured is primarily contributed by the transport of the target molecule across the target cell types. In some embodiments, in order to further minimize effect of other non-target cells contributing to the plasma membrane capacitance, changes to the PMc in response to the agent rather than absolute PMc can be determined. For example, as described earlier, a pancreatic islet comprises at least beta cells and alpha cells. These different cell types can contribute to the plasma membrane capacitance (PMc). However, glucose-dependent increase in PMc is predominantly due to β-cells, since α-cells reduce secretion of glucagon in response to high glucose. Accordingly, in some embodiments, glucose can be added to stimulate insulin secretion from beta-cells but reduce glucagon secretion from alpha cells, resulting in measuring increase in PMc primarily due to exocytosis of insulin. In some embodiments, to further minimize effect of α-cells, changes to the PMc in response to glucose rather than absolute PMc can be determined.

Impedance Spectroscopy and Equivalent Electric Circuit

Impedance spectroscopy (also known as dielectric spectroscopy or electrochemical impedance spectroscopy (EIS)) is an art-recognized experimental technique to measure the dielectric properties of a medium as a function of frequency. Impedance spectroscopy has been used to assess the electrical impedance properties of biological tissues (Dean et al., "Electrical Impedance Spectroscopy Study of Biological Tissues" J. Electrostat. 2008; 66: 165-177) and/or measure plasma membrane capacitance and exocytosis in single cells including erythrocytes, beta cells, and gamma cells, and/or measure exocytosis during sea urchin fertilization. See, e.g., Cole and Spencer, "Electrical impedance of fertilized *Arabica* egg suspension" 1938 J. General Physiol. 21: 583-590; Joshi and Fernandez, "Capacitance measurements: an analysis of the phase detector techniques used to study exocytosis and endocytosis" 1988 Biophys. J. 53: 885-892; Barnett and Misler, "An optimized approach to membrane capacitance estimation using dual-frequency excitation" 1997 Biophysical Journal 72: 1641-1658; Gopel et al., "Voltage-gated and resting membrane currents recorded from B-cells in intact mouse pancreatic islets" 1999 J Physiol. 521.3: 717-728; Gopel et al., "Patch-clamp characterization of somatostatin-secreting δ-cells in intact mouse pancreatic islets" 2000 J. Physiol. 528.3: 497-507; and Gopel et al., "Capacitance measurements of exocytosis in mouse pancreatic α-, β- and δ-cells within intact islets of Langerhans" 2004 J. Physiol. 556.3: 711-726. However, the impedance measurements described in the art were performed based on each individual cell (patch clamp method: one cell at a time to measure exocytosis), rather than on the entire population of cells as a whole, in which intercellular space between cells, and/or organization/arrangement of cells within the population can also contribute to the capacitance measurements. Thus, the patch clamp circuit model is very different from the equivalent electric circuit model of the methods described herein (e.g., but not limited to 3-element circuit model), which, in part, has a substantial extracellular conductance that will pass most of the DC and low frequency current. In addition, changes in membrane conductance during a patch clamp can severely limit the accuracy of the capacitance measurements. While impedance or dielectric spectroscopy has been used to calculate the dielectric properties, impedance or dielectric spectroscopy has not been previously used to monitor changes in plasma membrane capacitance during exocytosis.

In accordance with one aspect described herein, at least two alternating currents each with a different frequency are utilized in the impedance spectroscopy to determine plasma membrane capacitance of all cells within a population. In one embodiment, dual frequency impedance spectroscopy (DFIS) which utilizes two AC currents with different frequencies is employed. The approach to single-cell membrane capacitance estimation using dual-frequency excitation has been described in Barnett and Misler, "An optimized approach to membrane capacitance estimation using dual-frequency excitation" 1997 Biophysical Journal 72: 1641-1658. However, Barnett and Mislet does not teach or suggest estimation of an overall membrane capacitance of a population of cells using dual-frequency excitation.

FIG. 3 is a complex impedance plot (CIP) showing changes in impedance at one frequency before (blue) and after (red) addition of 25 mM KCl as an insulin secretagogue that produces substantial exocytosis of insulin from cells in the islet. The shift after addition of 25 mM KCl is due to exocytosis of insulin as well as an increase in the plasma membrane surface area and capacitance. The units on the complex impedance plot represent the impedance of the real (resistance) and imaginary (capacitance) properties of the pancreatic islets with relative units that have not been normalized to Ohms. In some embodiments where the secretagogue is less powerful to produce a detectable shift, a method with greater signal to noise that is not prone to interference when resistance in the circuit changes can be employed, e.g., using one or more embodiments of the method described herein, where at least two or more alternating currents with different frequencies can be applied to the population of cells.

Figure 4A:
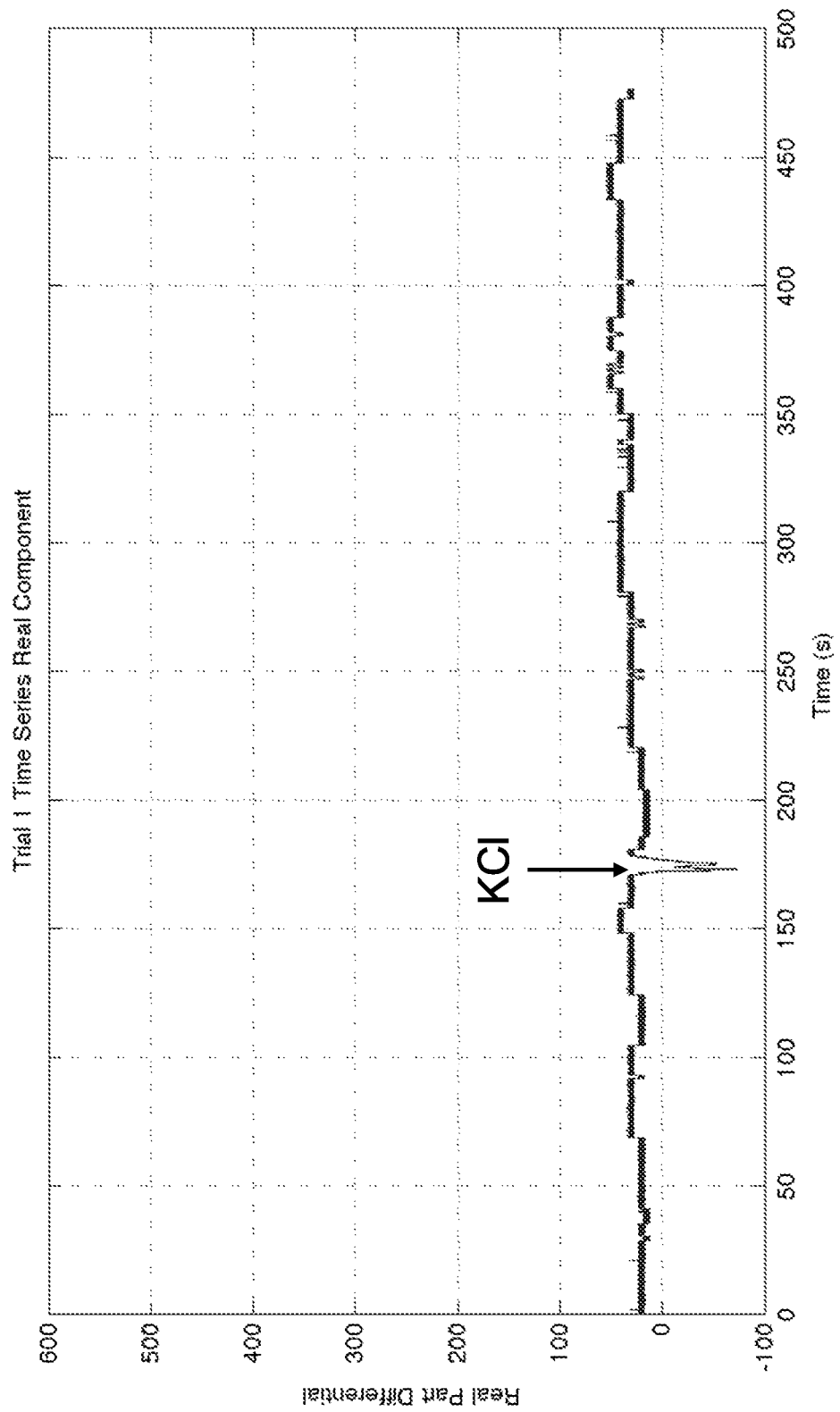
FIGS. 4A-4B is a set of time-series graphs showing real-time monitoring exocytotic activity of a pancreatic islet using a single frequency.
Figure 4B:
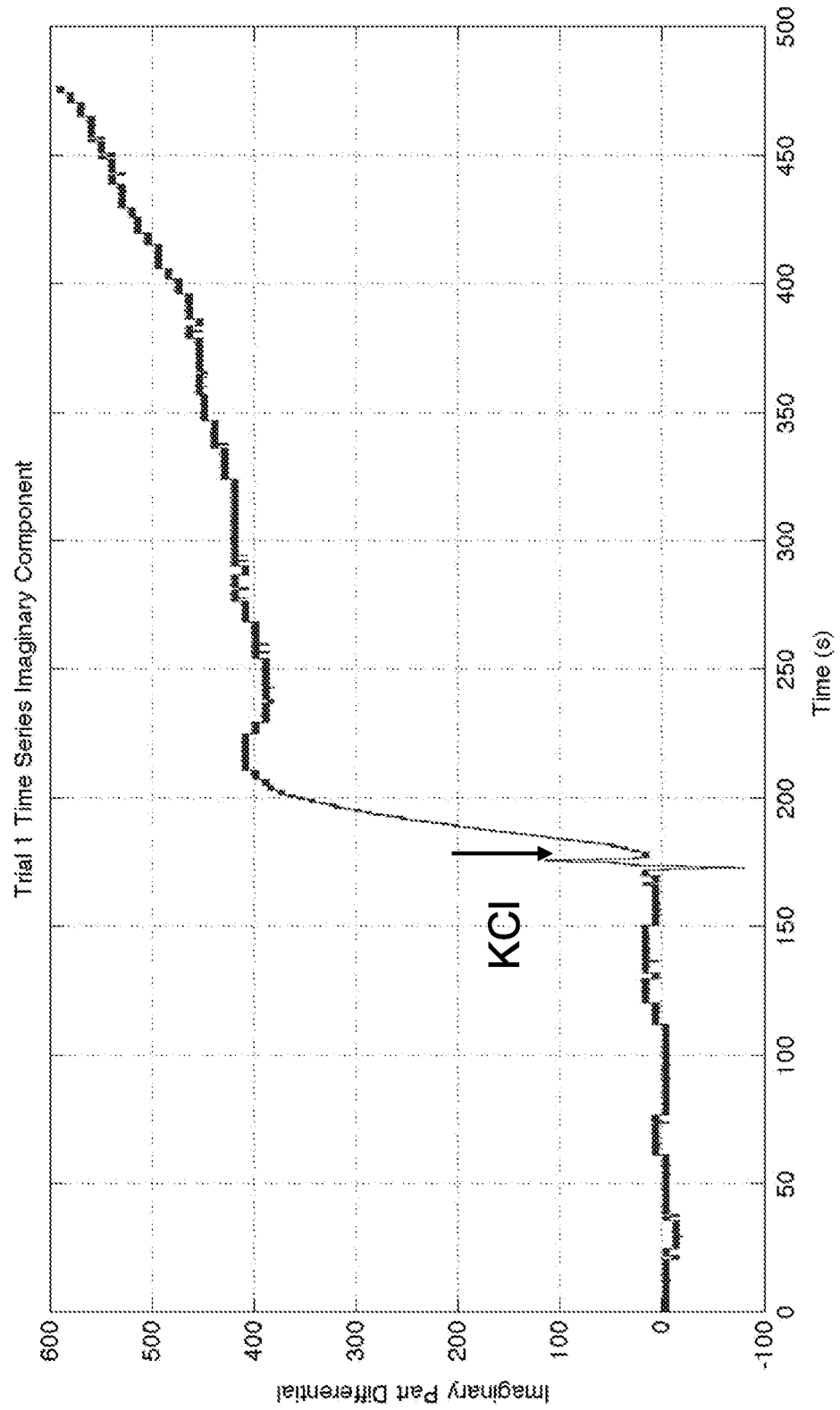
Figure 6:
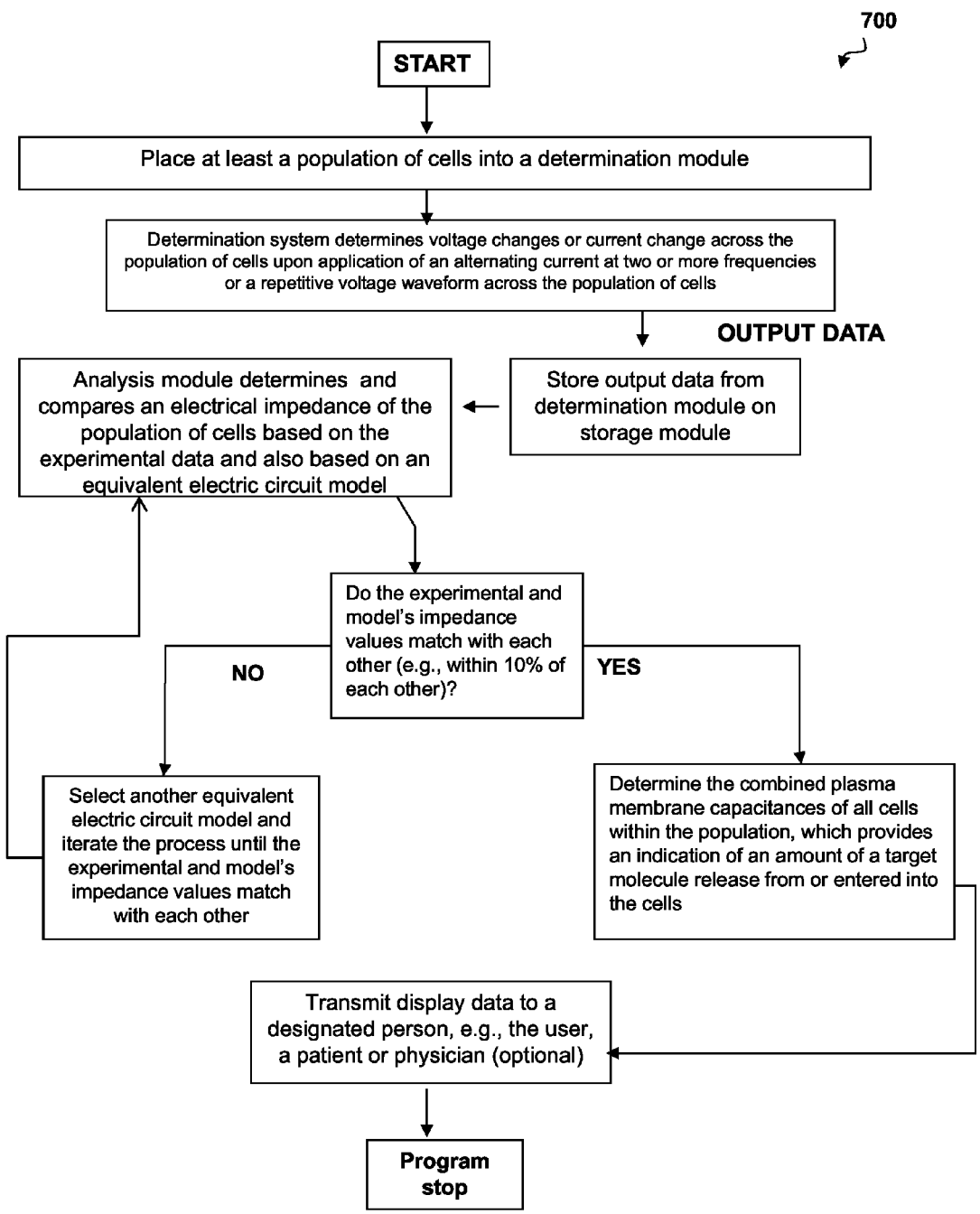
FIG. 6 is an exemplary set of instructions on a computer readable storage medium for use with the systems described herein.

FIGS. 4A-4B is a set of time-series graphs showing real-time monitoring exocytotic activity of a pancreatic islet using a single frequency. FIG. 4A is a graph of impedance measurements over time showing the real (whole islet resistance) component of the islet circuit. FIG. 4B is a graph of impedance measurements acquired at a frequency of ~1250 Hz over time showing the imaginary (whole islet capacitance) component of the islet circuit. In the beginning of the recording a background signal indicates inactive exocytotic activity of the islet. Addition of KCl to a final concentration of 25 mM leads to an immediate change in whole islet capacitance (FIG. 4B) but not whole islet resistance (FIG. 4A). The capacitance plateaus before starting another slight rise. The change in capacitance is directly proportional to the amount of insulin that this islet released.

Impedance spectroscopy data are generally analyzed in terms of an equivalent circuit model comprising a plurality of passive elements. As used herein, the term "passive elements" refers to elements of an electric circuit that do not create power, e.g., a capacitor, an inductance, a resistor or a memristor. An equivalent circuit model is selected such that its impedance matches the measured data.

The type of passive elements in an electric circuit model and their interconnections generally control the shape of the model's impedance spectrum. The model's parameters (e.g., the resistance value of a resistor and the capacitance of a capacitor) can control the size of each feature in the spectrum. Both these factors affect the degree to which the model's impedance spectrum matches with a measured spectrum by impedance spectroscopy.

In accordance with different aspects described herein, various components of the population of cells (including, e.g., plasma membranes, cytosolic space within the cells, and intercellular space between the cells) can contribute to electrical impedance of the population.

Impedance is represented as a complex quantity (z) and the term complex impedance may be used interchangeably; the polar form conveniently captures both magnitude and phase characteristics, where the magnitude represents the ratio of the voltage difference amplitude to the current amplitude, while the argument θ gives the phase difference between voltage and current. In Cartesian form, where the real part of impedance corresponds to the resistance R and the imaginary part corresponds to the capacitance C.

Impedance is used as the measurement of opposition to an alternating current. Mathematically, impedance is measured by the following equation, which is analogous to Ohm's law: $Z=V/I$ (1) where, voltage=V, current=I, and impedance=Z. An object that conducts electricity with unknown impedance can be determined from a simple circuit. Applying a known alternating current across an object while simultaneously measuring the voltage across the object and using equation (1) yields the impedance.

Various components of the population of cells (including, e.g., plasma membranes, cytosolic space within the cells, and intercellular space between the cells) can be modeled as a passive component (e.g., a resistor, a capacitor, or a combination thereof) in the equivalent electric circuit accordingly. Thus, the equivalent electric circuit used in modeling the population of cells for determination of its electrical impedance comprises a plurality of passive elements (e.g., at least one resistor, at least one capacitor, or any combination thereof). For example, in some embodiments, the plurality of passive elements can comprise at least one or more (e.g., 1, 2, 3, 4, 5, 6, or more) capacitors. In some embodiments, the equivalent electric circuit can further comprise at least one or more (e.g., 1, 2, 3, 4, 5, 6, or more) resistors.

Each single cell within the population can be modeled independently as a smaller electric circuit, which is then connected with others to form a complex equivalent electric circuit, or alternatively, the entire population of cells can be modeled as a whole entity.

In some embodiments of the methods and systems described herein, the entire population of cells can be modeled as a whole entity. For example, in some embodiments, at least one of the passive elements is a capacitor representing the combined plasma membrane capacitances of all cells in the population. In some embodiments, the combined plasma membrane capacitances of the population of cells can be modeled as a combination of a capacitor and a first resistor (e.g., connected in parallel to each other in the equivalent electric circuit). In some embodiments, the combined cytosolic space of the population of cells is modeled as a second resistor. In these embodiments, the second resistor can be connected in series with at least the capacitor (representing the plasma membrane capacitances) in the equivalent electric circuit. In some embodiments, the intercellular space of the population of cells can be modeled as a third resistor, e.g., which can be connected in parallel to the second resistor in the equivalent electric circuit. A change in impedance of the capacitor can reflect an amount of the target molecule released from or entered into the population of cells.

While the choice of which electric circuit model applies to a population of cells (e.g., one or more groups of cells, one or more cell clusters, one or more islets of cells, or one or more tissue samples) can generally be selected based on the physical characteristics of the population of cells (e.g., structural components of the cells), in some embodiments, an electric circuit model can also be partially or completely empirical in order to give the best possible match between the model's impedance and the measured impedance.

By way of example only, in one embodiment, the method can be used to measure exocytosis of a target molecule from an islet of cells. In one embodiment, weak AC currents (e.g., AC currents that do not significantly cause any adverse effect on the biological cells, e.g., cell viability) can be passed through an entire islet simultaneously under a current clamp (FIG. 1A). Islets can be modeled by at least 3 (e.g., 3, 4, 5, or more) passive elements as in the equivalent electric circuit. In one embodiment, islets can be modeled by 4 passive elements as in the equivalent electric circuit, where $R_{MEM}$ and $C_{MEM}$ represent the sum of the plasma membrane (MEM) resistances (R) and capacitances (C), and $R_{CYT}$ and $R_{INT}$ represent the sum of cytosolic (CYT) and intercellular space (INT) resistances, for all cells in the islet, respectively (FIG. 1B). AC currents applied across a whole islet result in voltage drops across these 4 elements, which are dependent, in part, on the AC frequency and the impedance (Z) of these elements ($V=I(Z_{R(MEM+CYR+INT)}+Z_{C(MEM)})$). For example, $Z_{C(MEM)}$ and $Z_{R(MEM)}$ are generally sensitive to the level of an applied secretagogue (e.g., glucose), which at stimulatory levels decrease the $R_{MEM}$, via opening of ion channels, and increase $C_{MEM}$, via surface area increase reflective of exocytosis. Separation of the measured AC voltage into real (in phase with current) and imaginary (out of phase with current) components for 2 different frequencies can provide direct determination of $R_{MEM}$, $C_{MEM}$, $R_{CYT}$ and $R_{INT}$ through generation of 4 separate equations.

Analysis of impedance spectroscopy data to determine impedance of the resistors and capacitors within an equivalent electric circuit are known in the art. In general, the impedance of resistors (e.g., first, second, or third resistor herein) can be determined from the first component of the measured voltage or current change that is in phase with the applied current or voltage waveform, respectively; while impedance of a capacitor can be determined from the second component of the measured voltage or current change that is out of phase with the applied current or voltage waveform, respectively.

Various circuit models can be used for fitting the impedance spectra data. Non-limiting examples of circuit models include the ones shown in Dean et al. "Electrical impedance spectroscopy study of biological tissues" 2008 J. Electrostat 66: 165-177, and the one described in FIG. 1B. In one embodiment, the circuit model as shown in FIG. 1B can be used. In alternative embodiments, the circuit model as shown in FIG. 1B can exclude $R_{MEM}$, when it turns out to be so high that substantially no current will pass through. Depending on electrical properties of different cell types and/or organization/structure of cells with a population or an islet, a circuit model can be modified accordingly, e.g., based on the complex impedance plots generated from impedance spectroscopy. For example, in some embodiments where a pancreatic islet is assayed, β-cells that are electrically coupled may indicate a larger resistor in series with the $R_{CYT}$ as shown in FIG. 1B. In these embodiments, as the resistance between cells may be likely greater than the resistances within a cell, $R_{CYT}$ may reflect the electrical resistance between β-cells rather than simply the cytosolic resistance. Thus, a circuit model can be modified, e.g., based on the complex impedance plots, to better account for $R_{CYT}$.

Without wishing to be bound by theory, the number of passive elements placed in an equivalent model generally determines the number of alternating currents required for use in one aspect of the methods described herein (based on application of an alternating current across a population of cells). For example, the use of two alternating currents at different frequencies provides for four equations (a pair—real and imaginary components—at each frequency), which can be used to determine the impedances of at least four passive elements. If more than four passive elements are used in an equivalent electric circuit model, in the aspect of the methods described herein where alternating currents are used, at least a third alternating current at a different frequency needs to be applied across a population of cells.

In one embodiment, the 3-passive element circuit model as shown in FIG. 1C can be used. The 3-passive element electric circuit can represent an equivalent circuit for a population of cells. The admittance (Y) of the equivalent 3-passive element circuit shown in FIG. 1C can be computed as follows in equation (1):

$$Y = \frac{R_{cyt}^2 \omega_1^2 C_{mem}^2 + R_{int} R_{cyt} \omega_1^2 C_{mem}^2 + 1}{R_{int}(R_{cyt}^2 \omega_1^2 C_{mem}^2 + 1)} + \frac{\omega_1 C_{mem}}{R_{cyt}^2 \omega_1^2 C_{mem}^2 + 1} j \quad (1)$$

wherein:
Y=admittance (defined as the inverse of impedance);
$R_{int}$ represents the resistance to current flow between cells (intercellular space);
$C_{mem}$ represents the capacitance of the plasma membranes;
$R_{cyt}$ represents the resistance of the cytosol; and
$\omega_1=2\pi f_1$ where $f_1$=frequency of one of the applied alternating or sinusoidal currents.

The imaginary part of equation (1) is generally used to derive $C_{mem}$ using alternating or sinusoidal currents applied at 2 different frequencies. The equation (2) below is the solution for membrane capacitance in real to near realtime while simultaneously applying two sinusoidal waveforms.

$$C_{(mem)} = \frac{I(1-k^2)}{\omega_1 k (V_1 k - V_2)} \quad (2)$$

wherein:
I is the applied current magnitude (the same) at two different frequencies;
$V_1$ and $V_2$ are the measured, out of phase, voltages (i.e. imaginary component) across the circuit from the applied currents at two different frequencies, respectively.
$\omega_2=2\pi f_2$ where $f_2$=frequency of the other applied alternating or sinusoidal current; and
$k=\omega_2/\omega_1=f_2/f_1$.

The accuracy of $C_{mem}$ can be increased with increasing frequency. Differences in $R_{int}$ and $R_{cyt}$ can produce predictable errors in $C_{mem}$ from the true $C_{mem}$. However, the relative change in $C_{mem}$ is generally unaffected at high frequencies and is proportional to the amount of exocytosis of a target molecule.

Target Molecule to be Detected by the Methods and Systems Described Herein

The methods and systems described herein can be used to detect exocytosis or endocytosis of any target molecule that is transported across cell membranes, and can cause a detectable change in the plasma membrane capacitance during the transport. Examples of a target molecule includes, but are not limited to, peptides, polypeptides, proteins, antibodies, antibody fragments (e.g., antigen binding fragments of antibodies), carbohydrate-binding protein, e.g., a lectin, glycoproteins, glycoprotein-binding molecules, amino acids, carbohydrates (including mono-, di-, tri- and poly-saccharides), lipids, steroids, hormones, lipid-binding molecules, cofactors, nucleosides, nucleotides, nucleic acids (e.g., DNA or RNA, analogues and derivatives of nucleic acids, or aptamers), peptidoglycan, lipopolysaccharide, small molecules, and any combinations thereof In some embodiments, the target molecule to be detected by the methods and systems described herein can be a secretory molecule produced in cells. In some embodiments, the target molecule to be detected by the methods and systems described herein can be a naturally-occurring or synthetic molecule to be introduced or uptaken by cells. In one embodiment, the target molecule can be a secretory hormone. Examples of a secretory hormone can include, but are not limited to, growth hormone (GH), adrenocorticotropic hormone (ACTH), thyroid-stimulating hormone (TSH), follicle-stimulating hormone (FSH), luteinizing hormone (LH), prolactin, melanocyte-stimulating hormone (MSH), antidiuretic hormone (ADH), oxytocin, thyroxin, calcitonin, parathyroid hormone (PTH), insulin, glucagon, somatostatin, aldosterone, cortisol, epinephrine, norepinephrine, thymosin, melatonin, estrogen, progesterone, testosterone, or any combinations thereof. In some embodiments, the methods and systems described herein can be used to detect exocytosis of insulin, glucagon, somatostatin, or any combinations thereof. In one embodiment, the methods and systems described herein can be used to detect exocytosis of insulin.

Population of Cells to be Assayed by the Methods and Systems Described Herein

The population of cells that are amenable to the methods and systems described herein can comprise one or more populations of single cells, one or more cell clusters, one or more islets of cells, one or more tissue samples, or any combinations thereof. The phrase "a population of cells" as used herein refers to one or more groups each comprising at least 2 or more cells, including, e.g., at least 3, at least 4, at least 5, at least 10, at least 20, at least 30, at least 40, at least 50, at least 100, at least 500, at least 1000, at least 2500, at least 5000, at least $1 \times 10^4$ cells or more.

The population of cells can comprise a biological cell selected from the group consisting of living cells (prokaryotic and eukaryotic, including mammalian), viruses, bacteria, fungi, yeast, protozoan, microbes, and parasites. The biological cell can be a normal cell or a diseased cell, e.g., a cancer cell. Mammalian cells include, without limitation; primate, human and a cell from any animal of interest, including without limitation; mouse, hamster, rabbit, dog, cat, domestic animals, such as equine, bovine, murine, ovine, canine, and feline. In some embodiments, the cells can be derived from a human subject. In other embodiments, the cells are derived from a domesticated animal, e.g., a dog or a cat. Exemplary mammalian cells include, but are not limited to, stem cells (e.g., naturally existing stem cells or derived stem cells), cancer cells, progenitor cells, immune cells, blood cells, fetal cells, and any combinations thereof. The cells can be derived from a wide variety of tissue types without limitation such as; hematopoietic, neural, mesenchymal, cutaneous, mucosal, stromal, muscle, spleen, reticuloendothelial, epithelial, endothelial, hepatic, kidney, gastrointestinal, pulmonary, cardiovascular, T-cells, and fetus. Stem cells, embryonic stem (ES) cells, ES-derived cells, induced pluripotent stem cells, and stem cell progenitors are also included, including without limitation, hematopoietic, neural, stromal, muscle, cardiovascular, hepatic, pulmonary, and gastrointestinal stem cells. Yeast cells may also be used as cells in some embodiments described herein. In some embodiments, the cells can be ex vivo or cultured cells, e.g. in vitro. For example, for ex vivo cells, cells can be obtained from a subject, where the subject is healthy and/or affected with a disease.

The population of cells can be derived from any tissue type from any species (e.g., animal, mammal, plant, and/or microbes). In some embodiments, the population of cells can comprise one or more of any cell types (e.g., but not limited to, somatic cells, stem cells (e.g., naturally existing stem cells or derived stem cells such as iPSCs), germ cells, bone marrow cells, adipose cells, dermal cells, epidermal cells, epithelial cells, connective tissue cells, fibroblasts, muscle cells, cartilage cells, chondrocytes, ocular cells, follicle cells, buccal cells, neuronal cells, reproductive cells, and/or blood cells), or of any tissue type (e.g., but not limited to, lung, liver, colon, heart, skin, brain, gastrointestinal, bone, pancreas and/or breast) from a mammalian subject, e.g., a human subject.

In one embodiment, the population of cells is derived from a pancreatic tissue. For example, the population of cells can comprise a pancreatic islet (e.g., an islet comprising a population of alpha cells, beta cells, and gamma cells), insulin-secreting beta cells, or insulin-secreting stem cells. The population of cells can be derived from any source, e.g., in vitro (e.g., cultured cells including, e.g., genetically-engineered cells), ex vivo, or in vivo. In some embodiments, the population of cells can be derived from a human subject.

The population of cells can comprise one or more cell types. By way of example only, a pancreatic islet subjected to the methods and systems described herein generally comprises more than one cell types, e.g., alpha cells producing glucagon (15-20% of total islet cells), beta cells producing insulin and amylin (65-80%), delta cells producing somatostatin (3-10%), PP cells (gamma cells) producing pancreatic polypeptide (3-5%), epsilon cells producing ghrelin (<1%). In another embodiment, a population of clonal cells subjected to the methods and systems described herein comprise one kind of cells. In some embodiments, a population of stem cells (e.g., but not limited to insulin-secreting stem cells) can comprise differentiated stem cells or stem cells at various differentiation states.

For a population of cells that comprise more than one different cell types contributing to the plasma membrane capacitance (PMc), in some embodiments, it is desirable to contact the population of cells with an agent specific for stimulating endocytosis or exocytosis of a target molecule and/or specific for stimulating target cells such that any change in the plasma membrane capacitance measured is primarily contributed by the transport of the target molecule across the target cell types. In some embodiments, in order to further minimize effect of other non-target cells contributing to the plasma membrane capacitance, changes to the PMc in response to the agent rather than absolute PMc can be determined. For example, as described earlier, a pancreatic islet comprises at least beta cells and alpha cells. These different cell types can contribute to the plasma membrane capacitance (PMc). However, glucose-dependent increase in PMc is predominantly due to β-cells, since α-cells reduce secretion of glucagon in response to high glucose. Accordingly, in some embodiments, glucose can be added to stimulate insulin secretion from beta-cells but reduce glucagon secretion from alpha cells, resulting in measuring increase in PMc primarily due to exocytosis of insulin. In some embodiments, to further minimize effect of α-cells, changes to the PMc in response to glucose rather than absolute PMc can be determined.

Systems, e.g., for Detecting Exocytosis of a Target Molecule from a Population of Cells Systems (e.g., a computer system) which can be employed in methods of various aspects described herein are also provided. In this aspect, the system comprises:
(a) at least one determination module configured to receive a population of cells and perform the following:
  i. applying a first alternating current with a first frequency across the population of cells;
  ii. applying a second alternating current with a second frequency across the population of cells;
  iii. measuring a first voltage change across the population of cells at the first frequency;
  iv. measuring a second voltage change across the population of cells at the second frequency; and (b) at least one storage device configured to store the first voltage change and the second voltage change determined from said determination module;
(c) at least one analysis module configured to determine an electrical impedance of the population of cells based 5 the measurements of the first voltage change and the second voltage change determined from the determination module, wherein a change in the electrical impedance of the population of cells indicates an amount of a target molecule released from or entered 10 into the population of cells; and
(d) at least one display module for displaying a content based in part on the analysis output from said analysis module, wherein the content comprises a signal indicative of the amount of the target molecule released from 15 or entered into the cells.

In some embodiments, said at least one analysis module can be further configured to compute a best-fitting line each for the measured first voltage change and the second voltage change by modeling the population of cells as an equivalent 20 electric circuit comprising a plurality of passive elements, wherein at least one of the passive elements is a capacitor representing sum of plasma membrane capacitances of all cells in the population, thereby determining at least a change in impedance of the capacitor provides an indication of an 25 amount of the target molecule released from or entered into the population of cells.

In some embodiments, said at least one analysis module can be further configured to separate the measured voltage change into a first component in phase with the applied 30 current and a second component out of phase with the applied current, wherein the first component of the measured voltage change corresponds to a voltage change across a resistor, and the second component of the measured voltage change corresponds to a voltage change across the capacitor. 35

In some embodiments, said at least one determination module can be configured to apply to the population of cells the first alternating current and second alternating current simultaneously. In alternative embodiments, said at least one determination module can be configured to apply to the 40 population of cells the first alternating current and second alternating current separately or sequentially. The frequency of the first alternating current and the second alternating current applied to the population of cells can be of any value, provided that exocytosis of a target molecule can be detected 45 at a selected frequency, e.g., a shift representing exocytosis is detectable in a complex impedance plot, e.g., as shown in FIG. 3. In one embodiment, an optimal frequency is selected when the largest shift (e.g., before and after stimulation with a secretagogue) is observed in the corresponding complex 50 impedance plot. In some embodiments, the frequency of the first alternating current and the second alternating current can range from about 10 Hz to about 10 MHz, or from about 100 Hz to about 1 MHz, or from about 1 kHz to about 1000 kHz. The optimal frequency of the alternating currents 55 applied to the population of cells can vary with a number of factors, including, but not limited to types and/or size of cell population, target molecule to be detected and/or potency of a secretagogue if added. The frequency of the first alternating current and the second alternating current applied to the 60 population of cells can be the same or different. For example, when the first alternating current and the second alternating current apply substantially the same frequency to the population of cells, it is contemplated that a more complex circuit model may be needed. Alternatively, when 65 the first alternating current and the second alternating current apply different frequencies to the population of cells, a simple electric circuit (e.g., but not limited to, a 3-passive element circuit model) can be used.

In some embodiments, said at least one storage device and/or said at least one analysis module can be configured to model at least one 3-passive element circuit as shown in FIG. 1C. The 3-passive element electric circuit can represent an equivalent circuit for a population of cells. The admittance (Y) of the equivalent 3-passive element circuit shown in FIG. 1C can be computed as follows in equation (1):

$$Y = \frac{R_{cyt}^2 \omega_1^2 C_{mem}^2 + R_{int} R_{cyt} \omega_1^2 C_{mem}^2 + 1}{R_{int}(R_{cyt}^2 \omega_1^2 C_{mem}^2 + 1)} + \frac{\omega_1 C_{mem}}{R_{cyt}^2 \omega_1^2 C_{mem}^2 + 1} j \quad (1)$$

wherein:
Y=admittance (defined as the inverse of impedance);
$R_{int}$ represents the resistance to current flow between cells (intercellular space);
$C_{mem}$ represents the capacitance of the plasma membranes;
$R_{CYT}$ represents the resistance of the cytosol; and
$\omega_1 = 2\pi f_1$ where $f_1$=frequency of one of the applied alternating or sinusoidal currents.

The imaginary part of equation (1) is generally used to derive $C_{mem}$ using alternating or sinusoidal currents applied at 2 different frequencies. The equation (2) below is the solution for membrane capacitance in real to near realtime while simultaneously applying two sinusoidal waveforms.

$$C_{(mem)} = \frac{I(1-k^2)}{\omega_1 k(V_1 k - V_2)} \quad (2)$$

wherein:
I is the applied current magnitude (the same) at two different frequencies;
$V_1$ and $V_2$ are the measured, out of phase, voltages (i.e. imaginary component) across the circuit from the applied currents at two different frequencies, respectively.
$\omega_2 = 2\pi f_2$ where $f_2$=frequency of the other applied alternating or sinusoidal current; and
$k = \omega_2/\omega_1 = f_2/f_1$.

The accuracy of $C_{mem}$ can be increased with increasing frequency. Differences in $R_{int}$ and $R_{cyt}$ can produce predictable errors in $C_{mem}$ from the true $C_{mem}$. However, the relative change in $C_{mem}$ is generally unaffected at high frequencies and is proportional to the amount of exocytosis of a target molecule.

A system based on application of a repetitive voltage waveform to a population of cells is also provided herein. The system comprises:
(a) at least one determination module configured to receive a population of cells and perform the following:
  i. applying a repetitive voltage waveform across the population of cells;
  ii. measuring a current change across the population of cells; and
(b) at least one storage device configured to store the current change determined from said determination module;
(c) at least one analysis module configured to determine an electrical impedance of the population of cells based the measurements of the current change determined from the determination module, wherein a change in the electrical impedance of the population of cells indicates an amount of a target molecule released from or entered into the population of cells; and (d) at least one display module for displaying a content based in part on the analysis output from said analysis module, wherein the content comprises a signal indicative of the amount of the target molecule released from or entered into the cells.

In some embodiments, said analysis module can be further configured to compute a best-fitting line for the measured current change by modeling the population of cells as an equivalent electric circuit comprising a plurality of passive elements, wherein at least one of the passive elements is a capacitor representing the sum of plasma membrane capacitances of all cells in the population, thereby determining a change in impedance of the capacitor provides an indication of an amount of the target molecule released from or entered into the population of cells.

In some embodiments, said analysis module can be further configured to separate the measured current change into a first component in phase with the applied voltage waveform and a second component out of phase with the applied voltage waveform, wherein the first component of the measured current change corresponds to a current change across a resistor, and the second component of the measured current change corresponds to a current change across the capacitor.

Any art-recognized voltage waveform can be generated in said at least one determination module and applied to the population of cells. In one embodiment, said at least one determination module can be configure to generate a repetitive voltage square waveform.

In some embodiments of the systems of various aspects described herein, said at least one determination module can be further configured to perform an act of contacting the population of cells with an agent identified for or being assessed for modulating exocytosis of the target molecule from the population of cells or endocytosis of the target molecule into the population of cells, e.g., prior to applying to a population of cells a alternating current at two or more frequencies or a repetitive voltage waveform.

In some embodiments where the population of cells is contacted with an agent, said at least one analysis module can be further configured to compare the electrical impedance of the population of cells with a control determined from the determination module or stored in the storage device, wherein a change in the electrical impedance of the population of cells from the control indicates an effect of the agent on modulating the exocytosis of the target molecule. In these embodiments, the content can further comprise a signal indicative of the agent selected for modulating exocytosis of the target molecule. In some embodiments, the agent can be identified for enhancing exocytosis of insulin, e.g., which can be used for treatment of diabetes in a subject.

In some embodiments, the change in the electrical impedance of the population of cells and/or the amount of the target molecule released from or entered into the cells as determined in the analysis module can provide assessment of viability of the population of cells. In these embodiments, the content can further comprise a signal indicative of viability of the population of cells.

In some embodiments where the population of cells is a pancreatic islet, the change in the electrical impedance of the pancreatic islet and/or the amount of insulin released from the pancreatic islet as determined in the analysis module can provide assessment of potency of the pancreatic islet. In these embodiments, the content can further comprise a signal indicative of the pancreatic islet recommended or not recommended for transplantation into a subject with diabetes.

A tangible and non-transitory (e.g., no transitory forms of signal transmission) computer readable medium having computer readable instructions recorded thereon to define software modules for implementing a method on a computer is also provided herein. In one embodiment, the computer readable storage medium comprises: (a) instructions for determining an electrical impedance of the population of cells based on the measurements of the first voltage change and the second voltage change determined from the determination module or stored in a storage device, wherein a change in the electrical impedance of the population of cells indicates an amount of a target molecule released from or entered into the population of cells; and (b) instructions for displaying a content based in part on the data output from the analysis module, wherein the content comprises a signal indicative of comprises a signal indicative of the amount of the target molecule released from or entered into the cells.

In another embodiment, the computer readable storage medium comprises: (a) instructions for determining an electrical impedance of the population of cells based on the measurements of the current change determined from the determination module or stored in a storage device, wherein a change in the electrical impedance of the population of cells indicates an amount of a target molecule released from or entered into the population of cells; and (b) instructions for displaying a content based in part on the data output from the analysis module, wherein the content comprises a signal indicative of comprises a signal indicative of the amount of the target molecule released from or entered into the cells.

Depending on the nature of the cell population and/or applications of the systems as desired by users, the computer readable storage medium can further comprise instructions for displaying additional content. In some embodiments where the population of cells is contacted with an agent, the content can further comprise a signal indicative of the agent selected for modulating exocytosis of the target molecule. In some embodiments, the agent can be identified for enhancing exocytosis of insulin, e.g., which can be used for treatment of diabetes in a subject. In some embodiments, the change in the electrical impedance of the population of cells and/or the amount of the target molecule released from or entered into the cells as determined in the analysis module can provide assessment of viability of the population of cells. In these embodiments, the content can further comprise a signal indicative of viability of the population of cells. In some embodiments where the population of cells is a pancreatic islet, the change in the electrical impedance of the pancreatic islet and/or the amount of insulin released from the pancreatic islet as determined in the analysis module can provide assessment of potency of the pancreatic islet. In these embodiments, the content can further comprise a signal indicative of the pancreatic islet recommended or not recommended for transplantation into a subject with diabetes.

In some embodiments, the computer readable storage medium can further comprise instructions to construct an equivalent electric circuit model in order to determine the model's impedance value, which can then be compared with the experimental impedance value.

Embodiments of the systems described herein have been described through functional modules, which are defined by computer executable instructions recorded on computer readable media and which cause a computer to perform method steps when executed. The modules have been segregated by function for the sake of clarity. However, it should be understood that the modules need not correspond to discrete blocks of code and the described functions can be carried out by the execution of various code portions stored on various media and executed at various times. Furthermore, it should be appreciated that the modules may perform other functions, thus the modules are not limited to having any particular functions or set of functions.

The computer readable media can be any available tangible media that can be accessed by a computer. Computer readable media includes volatile and nonvolatile, removable and non-removable tangible media implemented in any method or technology for storage of information such as computer readable instructions, data structures, program modules or other data. Computer readable media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

In some embodiments, the computer readable storage media 700 can include the "cloud" system, in which a user can store data on a remote server, and later access the data or perform further analysis of the data from the remote server.

Computer-readable data embodied on one or more computer-readable media, or computer readable medium 700, may define instructions, for example, as part of one or more programs, that, as a result of being executed by a computer, instruct the computer to perform one or more of the functions described herein (e.g., in relation to system 600, or computer readable medium 700), and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of system 600, or computer readable medium 700 described herein, may be distributed across one or more of such components, and may be in transition there between.

The computer-readable media can be transportable such that the instructions stored thereon can be loaded onto any computer resource to implement the assays and/or methods described herein. In addition, it should be appreciated that the instructions stored on the computer readable media, or computer-readable medium 700, described above, are not limited to instructions embodied as part of an application program running on a host computer. Rather, the instructions may be embodied as any type of computer code (e.g., software or microcode) that can be employed to program a computer to implement the assays and/or methods described herein. The computer executable instructions may be written in a suitable computer language or combination of several languages, e.g., MATLAB. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the system described herein can include a determination module, a storage device, an analysis module and a display module. The functional modules can be executed on one, or multiple, computers, or by using one, or multiple, computer networks. The determination module 602 can have computer executable instructions to perform impedance spectroscopy described herein, e.g., either by applying an alternating current at two or more frequencies or a repetitive voltage waveform across a population of cells.

Figure 2:
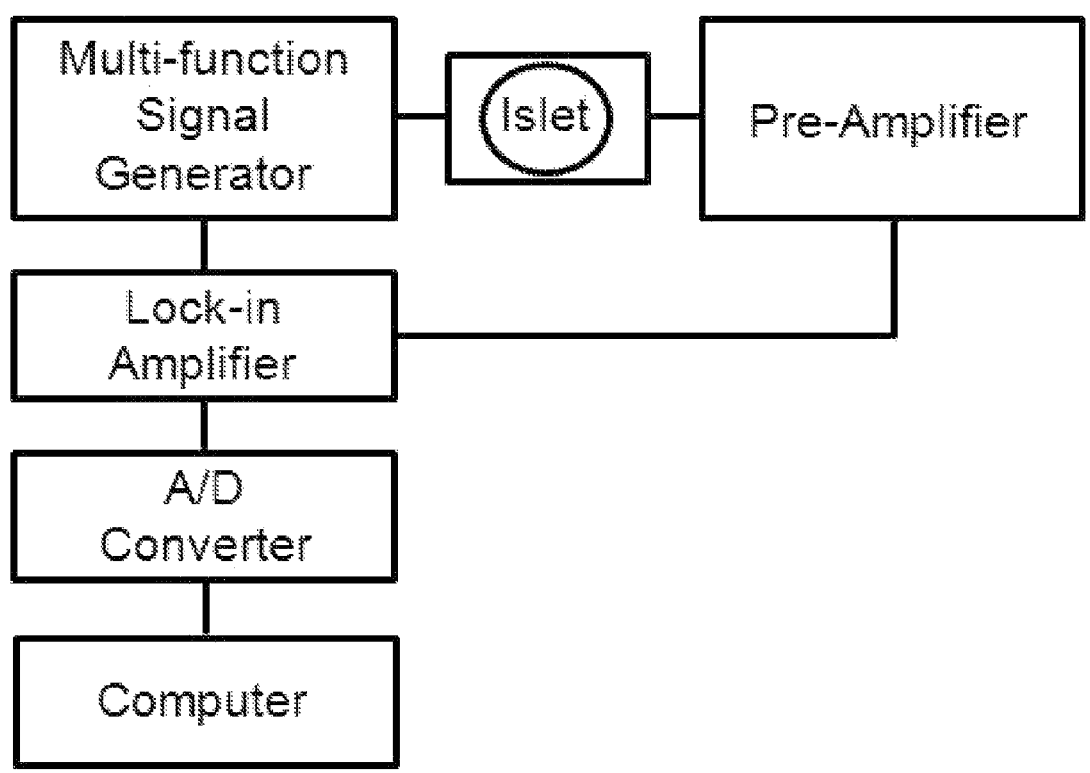
FIG. 2 is a block diagram for islet AC impedance. AC current is applied at two different frequencies (f1 and f2) to an islet (e.g., by a multi-function signal generator such as a dual channel function generator) and the voltage is fed to the waveforms and the measured voltage waveforms (e.g., by a pre-amplifier) are fed into a lock-in amplifier to separate the real and imaginary components before digitalizing (A/D converter) and feeding into a computer for near real-time analysis.

By way of example only, the two optimal AC frequencies are applied simultaneously to islets, e.g., according to the block diagram in FIG. 2. Individual electronic components and equipment for impedance spectroscopy are commercially available and known in the art. For example, a BK Precision #4078 dual channel function generator can be used to apply 2 known frequencies of AC to an islet as well as supply the reference waveform to the EG&G Instruments #7260 lock-in amplifier (LIA). An EG&G Instruments #5113 pre-amplifier can measure the voltage changes across the islet at both frequencies, amplify the signal and pass it back into the LIA for comparison with the reference waveforms. The EG&G LIA is digital and works as both the LIA and the A/D converter. It is capable of separating the real and imaginary parts of both input frequencies and passing those on to a computer, e.g., via an RS232 connection. The computer can be used to compute, track and store the values of the passive elements of the equivalent circuit corresponding to the islet being measured. In some embodiments, the method described herein can be automated, e.g., through computer control with as few external parts as possible.

The measured voltages changes or current changes across the population of cells determined in the determination module can be read by the storage device 604. As used herein the "storage device" 604 is intended to include any suitable computing or processing apparatus or other device configured or adapted for storing data or information. Examples of electronic apparatus suitable for use with the system described herein can include stand-alone computing apparatus, data telecommunications networks, including local area networks (LAN), wide area networks (WAN), Internet, Intranet, and Extranet, and local and distributed computer processing systems. Storage devices 604 also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. Such information may be provided in digital form that can be transmitted and read electronically, e.g., via the Internet, on diskette, via USB (universal serial bus) or via any other suitable mode of communication, e.g., the "cloud".

As used herein, "stored" refers to a process for encoding information on the storage device 604. Those skilled in the art can readily adopt any of the presently known methods for recording information on known media to generate manufactures comprising the sequence information or expression level information.

A variety of software programs and formats can be used to store the impedance spectroscopy data or spectrum (e.g., measured voltage changes or current change across the population of cells) the sequence information or expression level information on the storage device. Any number of data processor structuring formats (e.g., text file or database) can be employed to obtain or create a medium having recorded thereon the impedance spectroscopy data.

By providing impedance spectroscopy data or spectra (e.g., measured voltage changes or current change across the population of cells) in computer-readable form, one can use the impedance spectroscopy data or spectra (e.g., measured voltage changes or current change across the population of cells) in readable form in the analysis module 606 to perform analysis such as determination of an electrical impedance of the population of cells based the measurements of the first voltage change and the second voltage change or current change determined from the determination module, wherein a change in the electrical impedance of the population of cells indicates an amount of a target molecule released from or entered into the population of cells; best-fit of a series of measured voltage change or current change data; construction of an equivalent electric circuit model and/or matching of the model's impedance values to the experimental impedance values. The analysis made in computer-readable form provides a computer readable analysis result which can be processed by a variety of means. Content 608 based on the analysis result can be retrieved from the analysis module 606 to indicate the amount of the target molecule released from or entered into the population of cells.

In one embodiment, the storage device 604 to be read by the analysis module 606 can comprise control datasets representing population of cells not contacted with any agent to modulate endocytosis or exocytosis of a target molecule; equations of various passive elements for custom construction of an equivalent electric circuit model; and/or various models of an electric circuit that are commonly used and/or known in the art. Non-limiting examples of circuit models include the ones shown in Dean et al. "Electrical impedance spectroscopy study of biological tissues" 2008 J. Electrostat 66: 165-177, and the ones described in FIGS. 1B and 1C.

The "analysis module" 606 can use a variety of available software programs and formats to determine an electrical impedance of the population of cells based the impedance spectroscopy data/spectra (e.g., measurements of the first voltage change and the second voltage change or measurements of current change) determined from the determination module, wherein a change in the electrical impedance of the population of cells indicates an amount of a target molecule released from or entered into the population of cells.

In some embodiments, the "analysis module" 606 can use a variety of available software programs and formats to compute a best-fitting line for a series of voltage change or current change data determined from the determination module and/or stored in the storage device. Examples of data-fitting programs include, but are not limited to, MATLAB, many statistical packages such as R and numerical software such as the GNU Scientific Library, SciPy, OpenOpt, and any art-recognized regression and curve-fitting software programs.

The analysis module 606, or any other module of the system described herein, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web. Thus, in a particular embodiment, users can directly access data (via Hypertext links for example) residing on Internet databases using a HTML interface provided by Web browsers and Web servers. In another embodiment, users can directly access data residing on the "cloud" provided by the cloud computing service providers.

The analysis module 606 provides computer readable analysis result that can be processed in computer readable form by predefined criteria, or criteria defined by a user, to provide a content based in part on the analysis result that may be stored and output as requested by a user using a display module 610. The display module 610 enables display of a content 608 based in part on the analysis result for the user, wherein the content 608 can be a signal indicative of an amount of a target molecule released from or entered into a population of cells, viability and/or potency of a population of cells, a pancreatic islet or a population of stem cells recommended or not recommendation for transplantation into a subject, or any combinations thereof. Such signal, can be for example, a display of content on a computer monitor, a printed page of content from a printer, or a light or sound.

In various embodiments of the computer system described herein, the analysis module 606 can be integrated into the determination module 602.

In one embodiment, the content 608 based on the analysis result is displayed a on a computer monitor. In one embodiment, the content 608 based on the analysis result is displayed through printable media. The display module 610 can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content 608 based on the analysis result. It should be understood that other modules of the system described herein can be adapted to have a web browser interface. Through the Web browser, a user may construct requests for retrieving data from the analysis module. Thus, the user will typically point and click to user interface elements such as buttons, pull down menus, scroll bars and the like conventionally employed in graphical user interfaces. The requests so formulated with the user's Web browser are transmitted to a Web application which formats them to produce a query that can be employed to extract the pertinent information related to a test sample, e.g., display of an indication of exocytosis or endocytosis of a target molecule, or display of information based thereon. In one embodiment, the information of the control data is also displayed.

In any embodiments, the analysis module can be executed by a computer implemented software as discussed earlier. In such embodiments, a result from the analysis module can be displayed on an electronic display. The result can be displayed by graphs, numbers, characters or words. In additional embodiments, the results from the analysis module can be transmitted from one location to at least one other location. For example, the comparison results can be transmitted via any electronic media, e.g., internet, fax, phone, a "cloud" system, and any combinations thereof. Using the "cloud" system, users can store and access personal files and data or perform further analysis on a remote server rather than physically carrying around a storage medium such as a DVD or thumb drive.

The system 600, and computer readable medium 700, are merely illustrative embodiments, e.g., for detecting exocytosis or endocytosis of a target molecule from or into a population of cells and/or for use in the methods of various aspects described herein and is not intended to limit the scope of the inventions described herein. Variations of system 600, and computer readable medium 700, are possible and are intended to fall within the scope of the inventions described herein.

The modules of the machine, or used in the computer readable medium, may assume numerous configurations. For example, function may be provided on a single machine or distributed over multiple machines.

Applications of the Methods and Systems Described Herein

The methods and/or systems described herein can generally be used to detect transport of a target molecule across plasma membranes of cells within one or more populations (e.g., one or more cell clusters, one or more islets, one or more tissue samples). In some embodiments, the methods and/or systems described herein can be used to detect endocytosis of a target molecule into a population of cells. In some embodiments, the methods and/or systems described herein can be used to detect exocytosis of a target molecule from a population of cells. Both phenomena involve a change in membrane surface area. Since biological membranes have a capacitance per unit area of 1 µF/cm², the membrane capacitance is a useful, geometry-independent probe of surface area.

Not only can the methods and systems described herein be used for detecting exocytosis or endocytosis of a target molecule from or into a population of cells, in particular embodiments, the methods and systems described herein can also be adapted to assess and sort human pancreatic islets prior to transplantation, which can in turn advance islet transplantation procedures, and/or to screen for treatments of diabetes by monitoring functional release of insulin from islets upon exposure to a candidate agent.

Accordingly, in yet another aspect, methods for assessing viability of a population are provided herein, wherein the method comprises performing one or more embodiments of the methods described herein for detecting exocytosis of a target molecule from a population of cells.

A further aspect provides a method of treating a subject with diabetes comprising transplanting into the subject at least one islet determined to be potent based on assessment of release of insulin from the islet using one or more embodiments of the methods described herein.

Methods of identifying an agent for modulating exocytosis of a target molecule (e.g., a secretagogue) from cells are also provided herein. The method comprises (a) contacting a population of cells with a candidate agent; (b) performing one or more embodiments of the methods described herein to detect exocytosis of the target molecule from the population of cells; and (c) comparing the electrical impedance of the population of cells determined from step (b) with a control, wherein a change in the electrical impedance of the population of cells from the control indicates an effect of the candidate agent on modulating the exocytosis of the target molecule; thereby identifying the candidate agent for modulating the exocytosis of the target molecule from the cells.

In some embodiments, the methods of identifying a secretagogue can be used to identify an agent for enhancing exocytosis of insulin. For example, in these embodiments, the population of cells used for identifying an insulin secretagogue can be insulin-secreting cells such as a pancreatic islet, a population of beta cells, and/or insulin-secreting stem cells. In some embodiments, the selected insulin secretagogue can be used for treatment of diabetes in a subject.

Not only can the methods of various aspects described herein be used to monitor exocytosis of a molecule (e.g., insulin) from a whole islet of cells, the methods can also be used to identify changes in PM conductance that occur during electrical depolarization and repolarization of the PM. For example, without wishing to be bound by theory, changes in the impedance of $R_{MEM}$ can reflect the closed and open states of many ion channels that give rise to exocytosis including $K_{ATP}$, voltage-gated $Ca^{2+}$, $BK^+$, and $Cl^-$.

In some embodiments, the methods of various aspects described herein can be used to measure effect of inflammatory cytokines (INFCYT) and palmitate/glucose (GLT), 2 conditions associated with Type 2 diabetes (T2D), on oscillatory plasma membrane capacitance (PMc) in vitro, ex vivo or in vivo. By way of example only, in an animal model, the plasma membrane capacitance (PMc) measurements of control (untreated) rodent islets can be compared to those treated with inflammatory cytokines (INFCYT) and ~0.2 mM palmitate/~20 mM glucose (GLT), conditions associated with T2D. Following a 24 hr treatment, the average lag, oscillatory period and oscillatory regularity in PMc can be determined following a step increase in glucose concentration from basal (4 mM) to stimulatory (16 mM), for each condition (Control, INFCYT, GLT). Healthy islets (controls) should generally show step increases in PMc during islet insulin secretion by synchronized β-cells that correspond to pulsatile insulin secretion.

In mouse islets 30% of vesicle fusion events are full fusion events where the vesicle becomes part of the plasma membrane while the other 60% percent are kiss-and-run and stable fusion pore events. In human islets, 60% of fusion events are full fusion events and 40% are kiss-and-run and stable pore events. Kiss-and-run and stable fusion pore events lasted, on average, ~0.5 s and ~8.3 min in mice and ~5.3 s and ~7.6 min in human β-cells, respectively. This indicates substantial overlap of exocytosis with relatively long lasting increases in plasma membrane surface area that can sum together to produce larger changes in capacitance.

Being able to determine exocytosis from a whole islet can provide an understanding of the rate of membrane recovery (endocytosis) at the whole islet level for which there is not a lot of information. In some embodiments, substantial disruption in total exocytosis and differences in oscillatory periodicity and oscillatory regularity between INFCYT/GLT-treated and control islets can be detected. Without wishing to be bound by theory, oscillations in glucose-stimulated insulin secretion (monitored herein by impedance) can be mirrored by oscillations in intracellular free $Ca^{2+}$, and impairment in oscillatory $Ca^{2+}$ profile has been previously shown to follow INCYT and GLT treatment.

In addition to detection/quantification of exocytosis of a molecule (e.g., insulin) at a whole cell population (e.g., islet) level, some embodiments of the methods described herein can be used to provide a rapid, non-invasive assay to screen populations of cells (e.g., islets), e.g., for potency, responsiveness to a secretagogue of interest, and/or viability prior to experimentation and/or transplantation. In some embodiments, the methods described herein can be used to serve as a platform for screening drugs which modulate exocytosis of a target molecule (e.g., insulin exocytosis).

Some Selected Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±1%.

In one aspect, the present invention relates to the herein described compositions, methods, and respective component(s) thereof, as essential to the invention, yet open to the inclusion of unspecified elements, essential or not ("comprising"). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these As used herein, the term "small molecules" refers to natural or synthetic molecules including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

As used herein, the term "hormone" can refer to polypeptide hormones, which are generally secreted by glandular organs with ducts. Included among the hormones are, for example, growth hormone such as human growth hormone, N-methionyl human growth hormone, and bovine growth hormone; parathyroid hormone; thyroxine; insulin; proinsulin; relaxin; estradiol; androgens such as calusterone, dromostanolone propionate, epitiostanol, mepitiostane, or testolactone; prorelaxin; glycoprotein hormones such as follicle stimulating hormone (FSH), thyroid stimulating hormone (TSH), and luteinizing hormone (LH); prolactin, placental lactogen, mouse gonadotropin-associated peptide, gonadotropin-releasing hormone; inhibin; activin; mullerian-inhibiting substance; and thrombopoietin. As used herein, the term hormone includes proteins from natural sources or from recombinant cell culture and biologically active equivalents of the native-sequence hormone, including synthetically produced small-molecule entities and pharmaceutically acceptable derivatives and salts thereof.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1

Impedance Analysis of a Pancreatic Islet for Insulin Exocytosis

Insulin exocytosis is a process which transiently increases plasma membrane surface area. The plasma membrane (PM) functions in part as an electrical capacitor (~1 g/cm$^2$), and plasma membrane capacitance (PMc) is directly proportional to the area of the PM. Transient increases in PM surface area due to the fusion of insulin granules, and may be followed using electrical capacitance measurements and real-time measurement of PMc serves to monitor insulin vesicle fusion events in single β-cells. Typical measurement of PMc is currently performed by measurement of "impedance" (alternating current (AC) analog of direct current DC "resistance"). This method is applied invasively by whole cell voltage clamp via a single patch pipette, and can be performed on individual β-cells only. However, the single β-cell does not adequately reflect the behavior of the entire β-cell population in an islet, especially when considering the diseased state.

In contrast to the existing invasive single-cell patch clamp approach, presented herein is a novel method of detecting exocytosis of a molecule from a population of cells (e.g., a cell cluster, an islet of cells, or a small tissue) that can eliminate the need for the invasive patch clamp approach and single-cell limitation. In particular, in one aspect, the method described herein employs use of Dual Frequency Impedance Spectroscopy (DFIS) to determine impedance measurement of the entire population of cells (e.g., but not limited to, a whole islet). In one embodiment, the method can be used for real-time recording of whole islet insulin exocytosis. Impedance spectroscopy has been used to measure plasma membrane capacitance and exocytosis in populations of single cells including erythrocytes; however, the impedance measurements were usually performed based on each individual cells (patch clamp method: one cell at a time to measure exocytosis), rather than on the entire population of cells as a whole, in which intercellular space between cells, and/or organization/arrangement of cells within the population can also contribute to the capacitance measurements. Thus, the patch clamp circuit model is very different from the equivalent electric circuit model of the methods described herein (e.g., but not limited to 3-element circuit model), which, in part, has a substantial extracellular conductance that will pass most of the DC and low frequency current. In addition, changes in membrane conductance during a patch clamp can severely limit the accuracy of the capacitance measurements. While impedance or dielectric spectroscopy has been used to calculate the dielectric properties, impedance or dielectric spectroscopy has not been previously used to monitor changes in plasma membrane capacitance during exocytosis.

In accordance with one aspect described herein, at least two alternating currents each with a different frequency are utilized in the impedance spectroscopy. In one embodiment, DFIS which utilizes two AC currents with different frequencies is employed.

In one embodiment, the method can be used to measure exocytosis of a molecule from an islet of cells. For example, weak AC currents (e.g., AC currents that do not significantly cause any adverse effect on the biological cells, e.g., cell viability) can be passed through an entire islet simultaneously under a current clamp (FIG. 1A) Islets can be modeled by at least 3 (e.g., 3, 4, 5, or more) passive elements as in the equivalent electric circuit. In one embodiment, islets can be modeled by 4 passive elements as in the equivalent electric circuit, where $R_{MEM}$ and $C_{MEM}$ represent the sum of the plasma membrane (MEM) resistances (R) and capacitances (C), and $R_{CYT}$ and $R_{INT}$ represent the sum of cytosolic (CYT) and intercellular space (INT) resistances, for all cells in the islet, respectively (FIG. 1B). AC currents applied across a whole islet result in voltage drops across these 4 elements, which are dependent, in part, on the AC frequency and the impedance (Z) of these elements ($V=I(Z_{R(MEM+CYT+INT)}+Z_{C(MEM)})$. $Z_{C(MEM)}$ and $Z_{R(MEM)}$ are generally sensitive to the level of an applied secretagogue (e.g., glucose), which at stimulatory levels decrease the $R_{MEM}$, via opening of ion channels, and increase $C_{MEM}$, via surface area increase reflective of exocytosis. Separation of the measured AC voltage into real (in phase with current) and imaginary (out of phase with current) components for 2 different frequencies can provide direct determination of $R_{MEM}$, $C_{MEM}$, $R_{CYT}$ and $R_{INT}$ through generation of 4 separate equations.

In order to optimize the resolution for monitoring changes in $C_{MEM}$, an appropriate AC current can be applied at selected frequencies where the measured voltage drop across $C_{MEM}$ is readily detectable (e.g., where the measured voltage drop cross $C_{MEM}$ changes the most) during exocytosis. For example, 2 optimal AC frequencies can be identified as follows: Complex Impedance Plots (CIPs) are generated by graphing the magnitude of the real vs. the imaginary parts of the impedance for a range of applied AC frequencies to islets in the presence of a secretagogue of interest (e.g., glucose at a concentration of ~4 mM and ~16 mM). CIP can provide visualization of the changes in plasma membrane capacitance (PMc) over the range of applied frequencies, and thus the frequencies (e.g., 2 frequencies) at which the largest changes (e.g., the two largest changes) in plasma membrane capacitance can be determined as optimal AC frequencies.

The two optimal AC frequencies are then applied simultaneously to islets, e.g., according to the block diagram in FIG. 2. Individual electronic components and equipment for impedance spectroscopy are commercially available and known in the art. For example, a BK Precision #4078 dual channel function generator can be used to apply 2 known frequencies of AC to an islet as well as supply the reference waveform to the EG&G Instruments #7260 lock-in amplifier (LIA). An EG&G Instruments #5113 pre-amplifier can measure the voltage changes across the islet at both frequencies, amplify the signal and pass it back into the LIA for comparison with the reference waveforms. The EG&G LIA is digital and works as both the LIA and the A/D converter. It is capable of separating the real and imaginary parts of both input frequencies and passing those on to a computer, e.g., via an RS232 connection. The computer can be used to compute, track and store the values of the passive elements of the equivalent circuit corresponding to the islet being measured. In some embodiments, the method described herein can be automated, e.g., through computer control with as few external parts as possible.

Not only can the methods of various aspects described herein be used to monitor exocytosis of a molecule (e.g., insulin) from a whole islet of cells, the methods can also be used to identify changes in PM conductance that occur during electrical depolarization and repolarization of the PM. For example, without wishing to be bound by theory, changes in the impedance of $R_{MEM}$ can reflect the closed and open states of many ion channels that give rise to exocytosis including $K_{ATP}$, voltage-gated $Ca^{2+}$, $BK^+$, and $Cl^-$.

In some embodiments, the methods of various aspects described herein can be used to measure effect of inflammatory cytokines (INFCYT) and palmitate/glucose (GLT), 2 conditions associated with Type 2 diabetes (T2D), on oscillatory plasma membrane capacitance (PMc) in vitro, ex vivo or in vivo. By way of example only, in an animal model, the plasma membrane capacitance (PMc) measurements of control (untreated) rodent islets can be compared to those treated with inflammatory cytokines (INFCYT) and ~0.2 mM palmitate/~20 mM glucose (GLT), conditions associated with T2D. Following a 24 hr treatment, the average lag, oscillatory period and oscillatory regularity in PMc can be determined following a step increase in glucose concentration from basal (4 mM) to stimulatory (16 mM), for each condition (Control, INFCYT, GLT). Healthy islets (controls) should generally show step increases in PMc during islet insulin secretion by synchronized β-cells that correspond to pulsatile insulin secretion. In mouse islets 30% of vesicle fusion events are full fusion events where the vesicle becomes part of the plasma membrane while the other 60% percent are kiss-and-run and stable fusion pore events. In human islets, 60% of fusion events are full fusion events and 40% are kiss-and-run and stable pore events. Kiss-and-run and stable fusion pore events lasted, on average, ~0.5 s and ~8.3 min in mice and ~5.3 s and ~7.6 min in human β-cells, respectively. This indicates substantial overlap of exocytosis with relatively long lasting increases in plasma membrane surface area that can sum together to produce larger changes in capacitance. Being able to determine exocytosis from a whole islet can provide an understanding of the rate of membrane recovery (endocytosis) at the whole islet level for which there is not a lot of information. In some embodiments, substantial disruption in total exocytosis and differences in oscillatory periodicity and oscillatory regularity between INFCYT/GLT-treated and control islets can be detected. Without wishing to be bound by theory, oscillations in glucose-stimulated insulin secretion (monitored herein by impedance) can be mirrored by oscillations in intracellular free $Ca^{2+}$, and impairment in oscillatory $Ca^{2+}$ profile has been previously shown to follow INCYT and GLT treatment.

Rodent islets are comprised of ~70% β-cells, as well as α (~20%) and δ (~10%) cells, while α-to-β cell ratio is higher in human islets (~55% of β-cells versus ~40% of α cells). All these different cell types can contribute to the plasma membrane capacitance (PMc). However, glucose-dependent increase in PMc is predominantly due to β-cells, since α-cells reduce secretion of glucagon in response to high glucose. In some embodiments, to further minimize effect of α-cells, changes to the PMc in response to glucose rather than absolute PMc can be determined.

Various circuit models can be used for fitting the impedance spectra data. In one embodiment, the circuit model as shown in FIG. 1B can be used. In alternative embodiments, the circuit model as shown in FIG. 1B can exclude $R_{MEM}$, when it turns out to be so high that substantially no current will pass through. Depending on electrical properties of different cell types and/or organization/structure of cells with a population or an islet, a circuit model can be modified accordingly, e.g., based on the complex impedance plots generated from impedance spectroscopy. For example, in some embodiments where a pancreatic islet is assayed, β-cells that are electrically coupled may indicate a larger resistor in series with the $R_{CYT}$ as shown in FIG. 1B. In these embodiments, as the resistance between cells may be likely greater than the resistances within a cell, $R_{CYT}$ may reflect the electrical resistance between β-cells rather than simply the cytosolic resistance. Thus, a circuit model can be modified, e.g., based on the complex impedance plots, to better account for $R_{CYT}$.

FIG. 3 is a complex impedance plot (CIP) showing changes in impedance at one frequency before (blue) and after (red) addition of 25 mM KCl as an insulin secretagogue that produces substantial exocytosis of insulin from cells in the islet. The shift after addition of 25 mM KCl is due to exocytosis of insulin as well as an increase in the plasma membrane surface area and capacitance. The units on the complex impedance plot represent the impedance of the real (resistance) and imaginary (capacitance) properties of the pancreatic islets with relative units that have not been normalized to Ohms. In some embodiments where the secretagogue is less powerful to produce a detectable shift, a method with greater signal to noise that is not prone to interference when resistance in the circuit changes can be employed, e.g., using one or more embodiments of the method described herein, where at least two or more alternating currents with different frequencies can be applied to the population of cells.

FIGS. 4A-4B is a set of time-series graphs showing real-time monitoring exocytotic activity of a pancreatic islet using a single frequency. FIG. 4A is a graph of impedance measurements over time showing the real (whole islet resistance) component of the islet circuit. FIG. 4B is a graph of impedance measurements over time showing the imaginary (whole islet capacitance) component of the islet circuit. In the beginning of the recording a background signal indicates inactive exocytotic activity of the islet. Addition of KCl to a final concentration of 25 mM leads to an immediate change in whole islet capacitance (FIG. 4B) but not whole islet resistance (FIG. 4A). The units on the y-axis in FIGS. 4A-4B are listed as 10 times the percentage change in whole islet capacitance acquired at a frequency of ~1250 Hz. The capacitance plateaus before starting another slight rise. This real-time detection of capacitance has been repeated with reproducible results. The change in capacitance is directly proportional to the amount of insulin that this islet released.

In addition to detection/quantification of exocytosis of a molecule (e.g., insulin) at a whole cell population (e.g., islet) level, some embodiments of the methods described herein can be used to provide a rapid, non-invasive assay to screen populations of cells (e.g., islets), e.g., for potency, responsiveness to a secretagogue of interest, and/or viability prior to experimentation and/or transplantation. In some embodiments, the methods described herein can be used to serve as a platform for screening drugs which modulate exocytosis of a target molecule (e.g., insulin exocytosis).

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The following aspects of the disclosure are exemplary only and not intended to limit the scope of the disclosure.

1. A method of detecting exocytosis of a target molecule from a population of cells comprising: a. applying a first alternating current with a first frequency across the population of cells; b. applying a second alternating current with a second frequency across the population of cells; c. measuring a first voltage change across the population of cells at the first frequency; d. measuring a second voltage change across the population of cells at the second frequency; and e. determining an electrical impedance of the population of cells, wherein a change in the electrical impedance of the population of cells indicates an amount of the target molecule released from the population of cells.

2. The method of aspect 1, wherein said determining the electrical impedance of the population of cells comprises matching a best-fitting line each computed for the measured first voltage change and the second voltage change to a function described by an equivalent electric circuit modeling the population of cells, wherein the equivalent electric circuit comprises a plurality of passive elements and at least one of the passive elements is a capacitor representing sum of plasma membrane capacitances of all cells in the population, thereby determining at least a change in impedance of the capacitor provides an indication of an amount of the target molecule released from the population of cells.

3. The method of aspect 1 or 2, wherein said determining the electrical impedance of the population of cells comprises separating the measured voltage change into a first component in phase with the applied current and a second component out of phase with the applied current, wherein the first component of the measured voltage change corresponds to a voltage change across a resistor, and the second component of the measured voltage change corresponds to a voltage change across the capacitor.

4. The method of any of aspects 1-3, wherein the first alternating current and second alternating current are applied simultaneously.

5. The method of any of aspects 1-4, wherein the first alternating current and second alternating current are applied sequentially.

6. The method of any of aspects 1-5, wherein the second frequency is different from the first frequency.

7. The method of any of aspects 1-6, wherein the first frequency ranges from about 10 Hz to about 10 MHz.

8. The method of any of aspects 1-7, wherein the second frequency ranges from about 10 Hz to about 10 MHz.

9. A method of detecting exocytosis of a target molecule from a population of cells, the method comprising: a. applying a repetitive voltage waveform across the population of cells; b. measuring a current change across the population of cells; and c. determining an electrical impedance of the population of cells, wherein a change in the electrical impedance of the population of cells indicates an amount of the target molecule released from the population of cells.

10. The method of aspect 9, wherein said determining the electrical impedance of the population of cells comprises matching a best-fitting line computed for the measured current change to a function described by an equivalent electric circuit modeling the population of cells, wherein the equivalent electric circuit comprises a plurality of passive elements and at least one of the passive elements is a capacitor representing sum of plasma membrane capacitances of all cells in the population, thereby determining at least a change in impedance of the capacitor provides an indication of an amount of the target molecule released from the population of cells.

11. The method of aspect 9 or 10, wherein said determining the electrical impedance of the population of cells comprises separating the measured current change into a first component in phase with the applied voltage waveform and a second component out of phase with the applied voltage waveform, wherein the first component of the measured current change corresponds to a current change across a resistor, and the second component of the measured current change corresponds to a current change across the capacitor.

12. The method of any of aspects 9-12, wherein the repetitive voltage waveform is a repetitive voltage square waveform.

13. The method of any of aspects 1-12, further comprising contacting the population of cells with an agent identified for or being assessed for modulating exocytosis of the target molecule.

14. The method of any of aspects 1-13, wherein the target molecule comprises insulin, glucagon, somatostatin, or any combination thereof.

15. The method of any of aspects 1-14, wherein the population of cells comprise a population of single cells, a cell cluster, an islet of cells, a tissue, or any combinations thereof.

16. The method of aspect 15, wherein the population of cells comprise a pancreatic islet, beta cells, stem cells, or any combination thereof.

17. The method of aspect 16, wherein the pancreatic islet comprises alpha cells, beta cells, and gamma cells.

18. The method of any of aspects 1-17, wherein the plurality of passive elements further comprise at least two resistors.

19. The method of any of aspects 1-18, wherein combined plasma membranes of the population of cells are modeled as the capacitor.

20. The method of aspect 19, wherein combined plasma membranes of the population of cells are modeled as the capacitor in combination with a first resistor.

21. The method of aspect 20, wherein the capacitor and the first resistor are connected in parallel in the equivalent electric circuit.

22. The method of any of aspects 1-21, wherein combined cytosolic space of the population of cells is modeled as a second resistor.

23. The method of aspect 22, wherein the second resistor is connected in series with at least the capacitor in the equivalent electric circuit.

24. The method of any of aspects 1-23, wherein the intercellular space of the population of cells is modeled as a third resistor.

25. The method of aspect 24, wherein the third resistor is connected in parallel to the second resistor in the equivalent electric circuit.

26. The method of any of aspects 18-25, wherein impedance of said first, second or third resistor is determined from the first component of the measured voltage or current change that is in phase with the applied current or voltage waveform, respectively.

27. The method of any of aspects 2-26, wherein impedance of the capacitor is determined from the second component of the measured voltage or current change that is out of phase with the applied current or voltage waveform, respectively.

28. The method of any of aspects 1-27, wherein the population of cells is derived from a human subject.

29. A method of assessing viability of a population of cells comprising performing the methods of any of aspects 1-28.

30. A method of treating a subject with diabetes comprising transplanting into the subject at least one islet determined to be potent by assessing release of insulin from the islet using the methods of any of aspects 1-28.

31. A method of identifying an agent for modulating exocytosis of a target molecule from cells comprising: a. contacting a population of cells with a candidate agent; b. performing the methods of any of aspects 1-28 to detect exocytosis of the target molecule from the population of cells; and c. comparing the electrical impedance of the population of cells determined from step (b) with a control, wherein a change in the electrical impedance of the population of cells from the control indicates an effect of the candidate agent on modulating the exocytosis of the target molecule; thereby identifying the candidate agent for modulating the exocytosis of the target molecule from the cells.

32. The method of aspect 31, wherein the population of cells comprises an islet of pancreatic cells, beta cells, stems cells, or any combinations thereof.

33. The method of aspect 31 or 32, wherein the target molecule is insulin, glucagon, or somatostatin.

34. The method of any of aspects 31-33, wherein the agent is identified for enhancing exocytosis of insulin.

35. The method of aspect 34, wherein the agent is identified for treatment of diabetes in a subject.

36. A system comprising: (a) at least one determination module configured to receive a population of cells and perform the following: i. applying a first alternating current with a first frequency across the population of cells; ii. applying a second alternating current with a second frequency across the population of cells; iii. measuring a first voltage change across the population of cells at the first frequency; iv. measuring a second voltage change across the population of cells at the second frequency; and (b) at least one storage device configured to store the first voltage change and the second voltage change determined from said determination module; (c) at least one analysis module configured to determine an electrical impedance of the population of cells based the measurements of the first voltage change and the second voltage change determined from the determination module, wherein a change in the electrical impedance of the population of cells indicates an amount of a target molecule released from the population of cells; and (d) at least one display module for displaying a content based in part on the analysis output from said analysis module, wherein the content comprises a signal indicative of the amount of the target molecule released from the cells.

37. The system of aspect 36, wherein said at least one analysis module is further configured to match a best-fitting line each computed for the measured first voltage change and the second voltage change to a function described by an equivalent electric circuit modeling the population of cells, wherein the equivalent electric circuit comprises a plurality of passive elements and at least one of the passive elements is a capacitor representing sum of plasma membrane capacitances of all cells in the population, thereby determining at least a change in impedance of the capacitor provides an indication of an amount of the target molecule released from the population of cells.

38. The system of aspect 36 or 37, wherein said at least one analysis module is further configured to separate the measured voltage change into a first component in phase with the applied current and a second component out of phase with the applied current, wherein the first component of the measured voltage change corresponds to a voltage change across a resistor, and the second component of the measured voltage change corresponds to a voltage change across the capacitor.

39. The system of any of aspects 36-38, wherein the first alternating current and second alternating current are applied simultaneously.

40. The system of any of aspects 36-38, wherein the first alternating current and second alternating current are applied sequentially.

41. The system of any of aspects 36-40, wherein the second frequency is different from the first frequency.

42. The system of any of aspects 36-41, wherein the first frequency ranges from about 10 Hz to about 10 MHz.

43. The system of any of aspects 36-42, wherein the second frequency ranges from about 10 Hz to about 10 MHz.

44. A system comprising: (a) at least one determination module configured to receive a population of cells and perform the following: i. applying a repetitive voltage waveform across the population of cells; ii. measuring a current change across the population of cells; and (b) at least one storage device configured to store the current change determined from said determination module; (c) at least one analysis module configured to determine an electrical impedance of the population of cells based the measurements of the current change determined from the determination module, wherein a change in the electrical impedance of the population of cells indicates an amount of a target molecule released from the population of cells; and (d) at least one display module for displaying a content based in part on the analysis output from said analysis module, wherein the content comprises a signal indicative of the amount of the target molecule released from the cells.

45. The system of aspect 44, wherein said analysis module is further configured to match a best-fitting line computed for the measured current change to a function described by an equivalent electric circuit modeling the population of cells, wherein the equivalent electric circuit comprises a plurality of passive elements and at least one of the passive elements is a capacitor representing sum of plasma membrane capacitances of all cells in the population, thereby determining at least a change in impedance of the capacitor provides an indication of an amount of the target molecule released from the population of cells 46. The system of aspect 44 or 45, wherein said analysis module is further configured to separate the measured current change into a first component in phase with the applied voltage waveform and a second component out of phase with the applied voltage waveform, wherein the first component of the measured current change corresponds to a current change across a resistor, and the second component of the measured current change corresponds to a current change across the capacitor.

47. The system of any of aspects 44-46, wherein the repetitive voltage waveform is a repetitive voltage square waveform.

48. The system of any of aspects 36-47, wherein said at least one determination module is further configured to perform an act of contacting the population of cells with an agent identified for or being assessed for modulating exocytosis of the target molecule released from the population of cells.

49. The system of any of aspects 36-48, wherein the target molecule comprises insulin, glucagon, somatostatin, or any combination thereof.

50. The system of any of aspects 36-49, wherein the population of cells comprise a population of single cells, a cell cluster, an islet of cells, a tissue, or any combinations thereof.

51. The system of aspect 50, wherein the population of cells comprise a pancreatic islet, beta cells, stem cells, or any combination thereof.

52. The system of aspect 51, wherein the pancreatic islet comprises alpha cells, beta cells, and gamma cells.

53. The system of any of aspects 48-52, wherein said at least one analysis module is further configured to compare the electrical impedance of the population of cells with a control determined from the determination module or stored in the storage device, wherein a change in the electrical impedance of the population of cells from the control indicates an effect of the agent on modulating the exocytosis of the target molecule.

54. The system of aspect 53, wherein the content further comprises a signal indicative of the agent selected for modulating exocytosis of the target molecule.

55. The system of aspect 54, wherein the agent is identified for enhancing exocytosis of insulin.

56. The system of aspect 55, wherein the agent is identified for treatment of diabetes in a subject.

57. The system of any of aspects 36-56, wherein the change in the electrical impedance of the population of cells and/or the amount of the target molecule released from the cells provides assessment of viability of the population of cells.

58. The system of aspect 57, wherein the content further comprises a signal indicative of viability of the population of cells.

59. The system of any of aspects 36-58, wherein the population of cells is a pancreatic islet.

60. The system of aspect 59, wherein the change in the electrical impedance of the pancreatic islet and/or the amount of insulin released from the pancreatic islet provides assessment of potency of the pancreatic islet.

61. The system of aspect 60, wherein the content further comprises a signal indicative of the pancreatic islet recommended or not recommended for transplantation into a subject with diabetes.

62. The system of any of aspects 36-61, wherein the plurality of passive elements further comprise at least two resistors.

63. The system of any of aspects 36-62, wherein combined plasma membranes of the population of cells are modeled as the capacitor.

64. The system of aspect 63, wherein combined plasma membranes of the population of cells are modeled as the capacitor in combination with a first resistor.

65. The system of aspect 64, wherein the capacitor and the first resistor are connected in parallel in the equivalent electric circuit.

66. The system of any of aspects 36-65, wherein combined cytosolic space of the population of cells is modeled as a second resistor.

67. The system of aspect 66, wherein the second resistor is connected in series with at least the capacitor in the equivalent electric circuit.

68. The system of any of aspects 36-67, wherein the intercellular space of the population of cells is modeled as a third resistor.

69. The system of aspect 68, wherein the third resistor is connected in parallel to the second resistor in the equivalent electric circuit.

70. The system of any of aspects 64-69, wherein impedance of said first, second or third resistor is determined from the first component of the measured voltage or current change that is in phase with the applied current or voltage waveform, respectively.

71. The system of any of aspects 36-70, wherein impedance of the capacitor is determined from the second component of the measured voltage or current change that is out of phase with the applied current or voltage waveform, respectively.

72. The system of any of aspects 36-71, wherein the population of cells is derived from a human subject.

What is claimed is:

1. A method of detecting and measuring exocytosis of a target molecule comprising insulin, glucagon, somatostatin, or any combination thereof, from a population of cells that is known or suspected to produce the target molecule, derived from a human subject, the method comprising:
    a. applying a first electrical signal with a first frequency across the population of cells, the first electrical signal being either an alternating current or an alternating voltage;
    b. applying a second electrical signal with a second frequency across the population of cells, the second electrical signal being either an alternating current or an alternating voltage;
    c. measuring a first voltage change across the population of cells at the first frequency if the first electrical signal is an alternating current or measuring a first current change across the population of cells at the first frequency if the first electrical signal is an alternating voltage;
    d. measuring a second voltage change across the population of cells at the second frequency if the second electrical signal is an alternating current or measuring a second current change across the population of cells at the second frequency if the second electrical signal is an alternating voltage; and
    e. determining a change in an electrical impedance of the population of cells at each of the first frequency and the second frequency, wherein the changes in the electrical impedances of the population of cells indicate an amount of the target molecule released from the population of cells.

2. The method of claim 1, wherein said determining the change in the electrical impedance of the population of cells comprises matching a best-fitting line each computed for the measured first voltage change or first current change and the second voltage change or second current change to a function described by an equivalent electric circuit modeling the population of cells, wherein the equivalent electric circuit comprises a plurality of passive elements and at least one of the passive elements is a capacitor representing sum of plasma membrane capacitances of all cells in the population, thereby determining at least a change in impedance of the capacitor provides an indication of an amount of the target molecule released from the population of cells.

3. The method of claim 2, wherein impedance of the capacitor is determined by separating each measured voltage or current change into an in-phase component and an out-of-phase component, and determining the impedance of the capacitor according to the out-of-phase components.

4. The method of claim 1, wherein said determining electrical impedance of the population of cells comprises separating the measured voltage change into a first component in phase with the applied current and a second component out of phase with the applied current, wherein the first and second components are used to determine impedances of passive elements of a circuit modeling the population of cells.

5. The method of claim 1, wherein the first electrical signal and second electrical signal are applied simultaneously.

6. The method of claim 1, further comprising contacting the population of cells with an agent identified for or being assessed for modulating exocytosis of insulin.

7. The method of claim 1, wherein the population of cells comprises a pancreatic islet of cells.

8. The method of claim 1, wherein the population of cells comprises a population of cells derived from a pancreatic islet.

* * * * *